(12) United States Patent
Blouin et al.

(10) Patent No.: US 7,553,973 B2
(45) Date of Patent: *Jun. 30, 2009

(54) PHARMACEUTICAL COMPOUNDS

(75) Inventors: Marc Blouin, St-Lazare-de-Vaudreuil (CA); Erich L. Grimm, Baie d'Urfe (CA); Yves Gareau, Notre-Dame-de L'ile-Perrot (CA); Marc Gagnon, Montreal (CA); Helene Juteau, Montreal (CA); Sebastien Laliberte, Ile Perrot (CA); Bruce MacKay, Dollard-des-Ormeaux (CA); Richard Friesen, Kirkland (CA)

(73) Assignee: Merck Frosst Canada Ltd., Quebec (CA)

( * ) Notice: Subject to any disclaimer, the term of this patent is extended or adjusted under 35 U.S.C. 154(b) by 0 days.

This patent is subject to a terminal disclaimer.

(21) Appl. No.: 11/385,615

(22) Filed: Mar. 21, 2006

(65) Prior Publication Data

US 2007/0149579 A1    Jun. 28, 2007

Related U.S. Application Data

(60) Provisional application No. 60/664,317, filed on Mar. 23, 2005.

(51) Int. Cl.
*A01N 43/82* (2006.01)
*C07D 285/08* (2006.01)
*C07D 271/06* (2006.01)

(52) U.S. Cl. .................... 548/128; 548/133; 514/361; 514/363

(58) Field of Classification Search .................... None
See application file for complete search history.

(56) References Cited

U.S. PATENT DOCUMENTS

| 5,073,563 | A | 12/1991 | Frickel et al. |
| 5,414,006 | A | 5/1995 | Rendenbach-Mueller et al. |
| 5,424,320 | A | 6/1995 | Fortin et al. |
| 5,552,437 | A | 9/1996 | Delorme et al. |
| 5,968,959 | A | 10/1999 | Levijoki et al. |
| 6,265,421 | B1 | 7/2001 | Pystynen et al. |
| 6,538,022 | B1 | 3/2003 | Kaivola et al. |
| 2003/0232809 | A1 | 12/2003 | Terashita et al. |
| 2004/0043985 | A1 | 3/2004 | Hicks et al. |
| 2006/0116406 | A1 | 6/2006 | Gareau et al. |

FOREIGN PATENT DOCUMENTS

| CA | 1330998 | 7/1994 |
| CA | 2 125 824 | 7/2006 |
| EP | 0650964 A1 | 5/1995 |
| WO | WO 02/47723 A1 | 6/2002 |
| WO | WO 2004/108720 | 12/2004 |

OTHER PUBLICATIONS

Chawla et al., "Challenges in Polymorphism of Pharmaceuticals", Crips vol. 5, No. 1, Jan.-Mar. 2004 (4 pages).*
Newman et al., "Solid-state analysis of the active pharmaceutical ingredient in drug products", DDT vol. 8, No. 19, Oct. 2003, pp. 898-905.*
U.S. Appl. No. 12/215,499, filed Mar. 2006, Blouin et al.*
Chemcats Database, Accesion No.s 2005: 1477662 & 2005: 1477663.
Journal of Indian Chem Society (1981), 58(10), 1021-3.
HCAPLUS, AN 2002:465845; DN 137:24354 (English Language Abstract for WO 2002/47723).
2002-599486/64; (English Language Abstract for WO 2002/47723).
Pending U.S. Appl. No. 11/886,757, Blouin et al.

* cited by examiner

*Primary Examiner*—Golam M. M. Shameem
*Assistant Examiner*—Sun Jae Y Loewe
(74) *Attorney, Agent, or Firm*—Mollie M. Yang; Valerie J. Camara

(57) ABSTRACT

The instant invention provides compounds of Formula Ia which are leukotriene biosynthesis inhibitors.

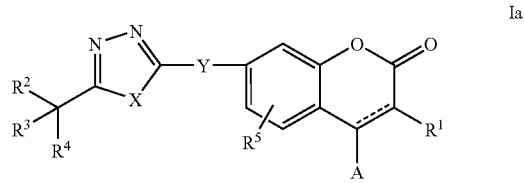

Compounds of Formula Ia are useful as anti-atherosclerotic, anti-asthmatic, anti-allergic, anti-inflammatory and cytoprotective agents.

19 Claims, No Drawings

PHARMACEUTICAL COMPOUNDS

CROSS REFERENCE TO RELATED APPLICATIONS

This application claims priority to U.S. Provisional Application No. 60/664,317, filed Mar. 23, 2005.

FIELD OF THE INVENTION

The instant invention involves novel compounds which are useful as inhibitors of leukotriene biosynthesis.

BACKGROUND OF THE INVENTION

Inhibition of leukotriene biosynthesis has been an active area of pharmaceutical research for many years. The leukotrienes constitute a group of locally acting hormones, produced in living systems from arachidonic acid. Leukotrienes are potent contractile and inflammatory mediators derived by enzymatic oxygenation of arachidonic acid by 5-lipoxygenase. One class of leukotriene biosynthesis inhibitors are those known to act through inhibition of 5-lipoxygenase (5-LO).

The major leukotrienes are Leukotriene $B_4$ (abbreviated as $LTB_4$), $LTC_4$, $LTD_4$ and $LTE_4$. The biosynthesis of these leukotrienes begins with the action of the enzyme 5-lipoxygenases on arachidonic acid to produce the epoxide known as Leukotriene $A_4$ ($LTA_4$), which is converted to the other leukotrienes by subsequent enzymatic steps. Further details of the biosynthesis as well as the metabolism of the leukotrienes are to be found in the book Leukotrienes and Lipoxygenases, ed. J. Rokach, Elsevier, Amsterdam (1989). The actions of the leukotrienes in living systems and their contribution to various diseases states are also discussed in the book by Rokach.

In general, 5-LO inhibitors have been sought for the treatment of allergic rhinitis, asthma and inflammatory conditions including arthritis. One example of a 5-LO inhibitor is the marketed drug zileuton (ZYLOFT®) which is indicated for the treatment of asthma. More recently, it has been reported that 5-LO may be an important contributor to the atherogenic process; see Mehrabian, M. et al., Circulation Research, 2002 Jul. 26, 91(2):120-126.

Despite significant therapeutic advances in the treatment and prevention of conditions affected by 5-LO inhibition, further treatment options are needed. The instant invention addresses that need by providing novel 5-LO inhibitors which are useful for inhibiting leukotriene biosynthesis.

SUMMARY OF THE INVENTION

The instant invention relates to compounds of Formula Ia which are leukotriene biosynthesis inhibitors, methods for their preparation, and methods and pharmaceutical formulations for using these compounds in mammals, especially humans.

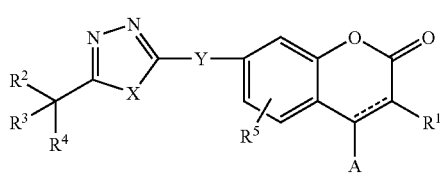

Ia

The compounds of Formula Ia are useful as pharmaceutical agents to slow or halt atherogenesis. Therefore, the instant invention provides a method for treating atherosclerosis, which includes halting or slowing the progression of atherosclerotic disease once it has become clinically evident, comprising administering a therapeutically effective amount of a compound of Formula Ia to a patient in need of such treatment. The instant invention also provides methods for preventing or reducing the risk of developing atherosclerosis and atherosclerotic disease events, comprising administering a prophylactically effective amount of a compound of Formula Ia to a patient who is at risk of developing atherosclerosis or having an atherosclerotic disease event.

Additionally, the instant invention involves the use of compounds of Formula Ia as anti-asthmatic, anti-allergic, anti-inflammatory and cytoprotective agents. They are also useful in treating angina, cerebral spasm, glomerular nephritis, hepatitis, endotoxemia, uveitis, and allograft rejection. The instant invention provides methods of treatment comprising administering a therapeutically effective amount of a compound of Formula Ia to a patient in need of the above-described treatments.

The instant invention further provides the use of a compound of Formula Ia in combination with other therapeutically effective agents. Additional embodiments will be evident from the following detailed description.

DETAILED DESCRIPTION OF THE INVENTION

The novel leukotriene biosynthesis inhibitors of the instant invention are compounds of structural Formula Ia

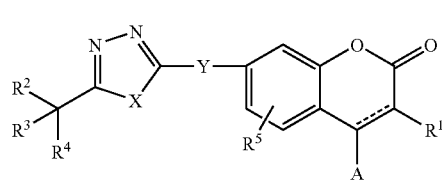

Ia and the pharmaceutically acceptable salts, esters and solvates thereof wherein ----- is selected from a single and a double bond;

"A" is selected from the group consisting of
(a) a 5-membered aromatic ring containing (i) one or more carbon atoms, (ii) one heteroatom selected from oxygen and sulfur, and (iii) zero, one, two or three nitrogen atoms,
(b) a 5-membered aromatic ring containing one or more carbon atoms and from one to four nitrogen atoms,
(c) a 6-membered aromatic ring containing carbon atoms and one, two or three nitrogen atoms;
(d) a bicyclic aromatic ring system selected from benzothienyl, indolyl, quinolinyl and naphthalenyl;
(e) phenyl, and
(f) —$CH_2$— phenyl;

and wherein A is optionally mono- or di-substituted with a substituent independently selected at each occurrence from the group consisting of (i) —F (ii) —Cl, (iii) —$C_{1-3}$alkyl optionally substituted with one or more of halo for example including —$CF_3$, (iv) —$OC_{1-3}$alkyl optionally substituted with one or more of halo for example including —$OCHF_2$ and —OCF$_3$, (v) —OC$_{3-6}$cycloalkyl, (vi) —CH$_2$OH, (vii) —COOR$^1$, (viii) —CN and (ix) —NR$^{10}$R$^{11}$;

X is selected from —O— and —S—;

Y is selected from:
(a) —NR$^6$—CHR$^7$ and —NR$^8$—C(O)— wherein the nitrogen in Y is linked to the 5-membered heterocyclic moiety of Formula Ia and the carbon in Y is linked to the bicyclic heterocyclic moiety of Formula Ia;
(b) —S—, —S(O) and —S(O)$_2$—, and
(c) —O—;

R$^1$ is selected from the group consisting of —H, —C$_{1-6}$ alkyl and —C$_{3-6}$ cycloalkyl;

R$^2$ is selected from the group consisting of —H, —OH, —F, —C$_{1-3}$alkyl, —OC$_{1-3}$alkyl and —OC(O)—C$_{1-3}$alkyl;

R$^3$ is selected from the group consisting of —H, —C$_{1-6}$alkyl, —C$_{1-6}$alkyl substituted with one or more of fluoro including for example but not limited to —C$_{1-6}$perfluoroalkyl such as —CF$_3$ and —CF$_2$CF$_3$, —C$_{1-6}$alkyl substituted with R$^9$, —C$_{2-6}$alkenyl, —C$_{3-6}$cycloalkyl, —C$_{5-7}$cycloalkenyl and -Z;

R$^4$ is selected from the group consisting of —H, —C$_{1-6}$alkyl, —C$_{1-6}$alkyl substituted with one or more of fluoro including for example but not limited to —C$_{1-6}$perfluoroalkyl such as —CF$_3$ and —CF$_2$CF$_3$, —C$_{1-6}$alkyl substituted with R$^9$, —C$_{2-6}$alkenyl, —C$_{3-6}$cycloalkyl, —C$_{5-7}$cycloalkenyl and -Z;

or R$^3$ and R$^4$ together represent oxo;

or R$^3$ and R$^4$ are joined together with the carbon to which they are attached to form a ring selected from the group consisting of a —C$_{3-6}$cycloalkyl ring and a —C$_{5-7}$cycloalkenyl ring, provided that when R$^3$ and R$^4$ are joined together with the carbon to which they are attached to form a —C$_{5-7}$cycloalkenyl ring, there is no double bond at the C-1 position in the ring;

or R$^2$, R$^3$ and R$^4$ are joined together with the carbon to which they are attached to form a cycloalkenyl ring selected from:

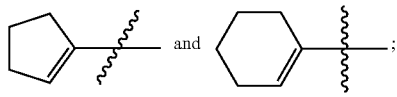

R$^5$ is absent or is a substituent selected from the group consisting of —C$_{1-6}$ alkyl, —C$_{3-6}$ cycloalkyl and halo;

R$^6$ is selected from the group consisting of (a) —H, (b) —C$_{1-4}$ alkyl, (c) —C(O)C$_{1-4}$ alkyl, and (d) —C(O)phenyl optionally substituted with —C$_{1-4}$ alkyl;

R$^7$ is selected from the group consisting of (a) —H, (b) —C$_{1-4}$ alkyl, (c) —C$_{3-6}$cycloalkyl, (d) phenyl optionally mono- or di-substituted with a substituent independently selected at each occurrence from the group consisting of —C$_{1-4}$ alkyl, —F and —Cl, and (e) a 5-membered aromatic ring containing (i) one or more carbon atoms, (ii) one heteroatom selected from oxygen and sulfur, and (iii) zero, one, two or three nitrogen atoms;

R$^8$ is selected from the group consisting of —H and —C$_{1-4}$ alkyl;

R$^9$ is selected from the group consisting of —COOR$^1$, —C(O)H, —CN, —CR$^1$R$^1$OH, —OR$^1$, —S—C$_{1-6}$alkyl and —S—C$_{3-6}$ cycloalkyl;

R$^{10}$ is selected from the group consisting of —H, —C$_{1-6}$ alkyl, —C$_{3-6}$ cycloalkyl and —COOR$^1$;

R$^{11}$ is selected from the group consisting of —H, —C$_{1-6}$ alkyl and —C$_{3-6}$ cycloalkyl; and Z is selected from the group consisting of
(a) a 5-membered aromatic ring containing (i) one or more carbon atoms, (ii) one heteroatom selected from oxygen and sulfur, and (iii) zero, one, two or three nitrogen atoms,
(b) a 5-membered aromatic ring containing one or more carbon atoms and from one to four nitrogen atoms,
(c) a 6-membered aromatic ring containing carbon atoms and one, two or three nitrogen atoms;
(d) phenyl, and
(e) —CH$_2$— phenyl and —CH$_2$-dioxolanyl, and wherein Z is optionally mono- or di-substituted with a substituent independently selected at each occurrence from the group consisting of (i) —F, (ii) —Cl, (iii) —C$_{1-3}$alkyl optionally substituted with one or more of halo for example including —CF$_3$, (iv) —OC$_{1-3}$alkyl optionally substituted with one or more of halo, (v) —OC$_{3-6}$cycloalkyl, (vi) —CH$_2$OH, (vii) —COOR$^1$, (viii) —CN and (ix) —NR$^{10}$R$^{11}$.

In one embodiment of this invention are compounds within the scope of Formula Ia having structural Formula Ib:

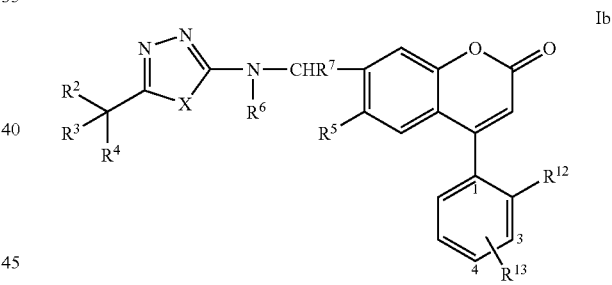

Ib and the pharmaceutically acceptable salts, esters and solvates thereof wherein R$^{12}$ is selected from the group consisting of —H and —F;

R$^{13}$ is absent or is a substituent at the 3- or 4-position and is selected from the group consisting of (i) —F, (ii) —Cl, (iii) —C$_{1-3}$alkyl optionally substituted with one or more of halo for example including —CF$_3$, (iv) —OC$_{1-3}$alkyl optionally substituted with one or more of halo for example including —OCHF$_2$ and —OCF$_3$, (v) —OC$_{3-6}$cycloalkyl, (vi) —CH$_2$OH, (vii) —COOR$^1$, (viii) —CN and (ix) —NR$^{10}$R$^{11}$; and the remaining variables are as defined in Formula Ia. In a class of this embodiment, R$^{13}$ is selected from the group consisting of —F, —OCF$_3$, —OCHF$_2$, —CN, —CH$_3$ and —OCH$_3$, and in a sub-class R$^{13}$ is —F.

In another class of this embodiment are compounds within the scope of Formula Ib having the following structural Formula I:

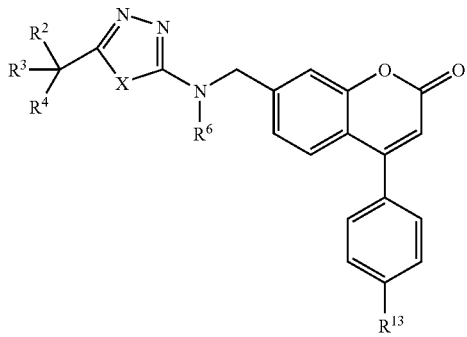

and the pharmaceutically acceptable salts, esters and solvates thereof wherein the variables present in Formula I are as defined in Formula Ib.

In another embodiment of this invention are compounds within the scope of Formula Ia, having structural Formula Ic:

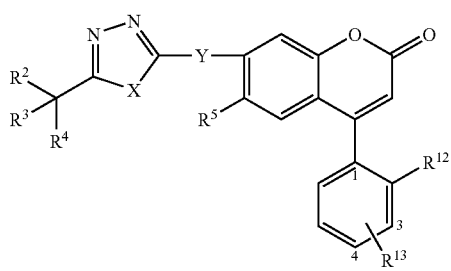

and the pharmaceutically acceptable salts, esters and solvates thereof wherein

Y is selected from —S— and —O—;

$R^{12}$ is selected from the group consisting of —H and —F;

$R^{13}$ is absent or is a substituent at the 3- or 4-position and is selected from the group consisting of (i) —F, (ii) —Cl, (iii) —$C_{1-3}$alkyl optionally substituted with one or more of halo for example including —$CF_3$, (iv) —$OC_{1-3}$alkyl optionally substituted with one or more of halo for example including —$OCHF_2$ and —$OCF_3$, (v) —$OC_{3-6}$cycloalkyl, (vi) —$CH_2OH$, (vii) —$COOR^1$, (viii) —CN and (ix) —$NR^{10}R^{11}$; and the remaining variables are as defined in Formula Ia. In a class of this embodiment, $R^{13}$ is selected from the group consisting of —F, —$OCF_3$, —$OCHF_2$, —CN, —$CH_3$ and —$OCH_3$, and in a sub-class $R^{13}$ is —F.

In another embodiment of this invention are compounds of Formula Ia wherein A is selected from the group consisting of:

a) a 5-membered aromatic ring containing (i) one or more carbon atoms, (ii) one heteroatom selected from oxygen and sulfur, and (iii) zero, one, two or three nitrogen atoms, b) a 5-membered aromatic ring containing one or more carbon atoms and from one to four nitrogen atoms, c) a 6-membered aromatic ring containing carbon atoms and one, two or three nitrogen atoms, and d) phenyl, and wherein A is unsubstituted, mono- or di-substituted as described in Formula Ia. In a class of this embodiment, A is unsubstituted, mono- or di-substituted as described in Formula Ia, and is selected from the group consisting of thienyl, furanyl, oxazolyl, thiazolyl, tetrazolyl, pyridinyl and phenyl, and particularly thiazolyl, pyridinyl and phenyl. In a sub-class of this embodiment, A is selected from phenyl, optionally substituted at the 3- or 4-position with a substituent selected from —F, —$OCF_3$, —$OCHF_2$, —CN, —$CH_3$ and —$OCH_3$, and optionally substituted at the 2-position with —F. More particularly, A is 4-fluoro-phenyl.

In another embodiment of this invention are compounds of Formula Ia, Ib, Ic and I wherein X is —S—. In another embodiment are compounds of Formula Ia, Ib, Ic and I wherein X is —O—.

In another embodiment of this invention are compounds of Formula Ia wherein Y is selected from —$NR^6$—$CHR^7$ and —$NR^8$—C(O)—. In a class of this embodiment Y is —$NR^6$—$CHR^7$—, and in a sub-class Y is —$NR^6$—$CH_2$—. In another embodiment are compounds of Formula Ia wherein Y is selected from —S— and —O—.

In another embodiment of this invention are compounds of Formula Ia wherein "-----" is a double bond.

In another embodiment of this invention are compounds of Formula Ia wherein $R^1$ is selected from —H and —$C_{1-6}$alkyl. In a class of this embodiment, $R^1$ is selected from —H and —$CH_3$, and in a further sub-class, $R^1$ is —H.

In another embodiment of this invention are compounds of Formulas Ia, Ib, Ic and I wherein $R^2$ is selected from the group consisting of —H, —OH, —F, —$C_{1-3}$alkyl, —$OCH_3$, and —OC(O)$CH_3$. In a class of this embodiment, $R^2$ is selected from —H and —OH, and more particularly it is —OH.

In another embodiment of this invention are compounds of Formulas Ia, Ib, Ic and I wherein $R^3$ is selected from the group consisting of —H, —$C_{1-6}$alkyl, —$C_{1-6}$alkyl substituted with one or more of fluoro, —$C_{3-6}$cycloalkyl and phenyl. In a class of this embodiment, $R^3$ is selected from —$CH_3$, —$C_2H_5$, —$C_{1-2}$alkyl substituted with fluoro particularly —$CF_3$ and —$CF_2CF_3$, and cyclopropyl.

In another embodiment of this invention are compounds of Formulas Ia, Ib, Ic and I wherein $R^4$ is selected from the group consisting of —H, —$C_{1-6}$alkyl, —$C_{1-6}$alkyl substituted with one or more of fluoro, —$C_{1-6}$alkyl substituted with $R^9$, and —$C_{3-6}$cycloalkyl. In a class of this embodiment, $R^4$ is selected from —$CH_3$, —$C_2H_5$, —$C_{1-2}$alkyl substituted with fluoro particularly —$CF_3$ and —$CF_2CF_3$, cyclopropyl and —$CH_2COOC_{1-4}$alkyl.

In another embodiment of this invention are compounds of Formulas Ia, Ib, Ic and I wherein $R^3$ and $R^4$ together represent oxo, or $R^3$ and $R^4$ together with the carbon to which they are attached represent a —$C_{3-6}$cycloalkyl ring.

In another embodiment of this invention are compounds of Formulas Ia, Ib and Ic wherein $R^5$ is selected from —H, —$CH_3$, —F and —Cl. In a class of this embodiment, $R^5$ is selected from —H and —$CH_3$.

In another embodiment of this invention are compounds of Formulas Ia, Ib and I wherein $R^6$ is selected from the group consisting of —H, —$CH_3$ and —$COCH_3$. In a class of this embodiment, $R^6$ is —H.

In another embodiment of this invention are compounds of Formulas Ia and Ib wherein $R^7$ is selected from the group consisting of —H and —$C_{1-4}$ alkyl. In a subclass of this embodiment, $R^7$ is —H.

In another embodiment of this invention are compounds of Formula Ia wherein $R^8$ is —H.

In another embodiment of this invention are compounds of Formulas Ia, Ib, Ic and I wherein $R^9$ is —COOR$^1$, and particularly —COOC$_{1-6}$alkyl.

In another embodiment of this invention are compounds of Formulas Ia, Ib, Ic and I wherein $R^{10}$ is selected from —H and —C$_{1-6}$ alkyl.

In another embodiment of this invention are compounds of Formulas Ia, Ib, Ic and I wherein $R^{11}$ is selected from —H and —C$_{1-6}$ alkyl.

In another embodiment of this invention are compounds of Formulas Ia, Ib, Ic and I wherein Z is unsubstituted, mono- or di-substituted as described in Formula Ia and is selected from the group consisting of phenyl, benzyl, pyridinyl, thiazolyl, dioxolanyl and tetrazolyl. In a class of this embodiment, Z is unsubstituted, mono- or di-substituted and is selected from the group consisting of phenyl, pyridinyl and thiazolyl.

Compounds of this invention include but are not limited to the following:

4-bromo-N-{[4-(4-fluorophenyl)-2-oxo-2H-chromen-7-yl]methyl}-N-{5-[1-hydroxy-1-(trifluoromethyl)propyl]-1,3,4-oxadiazol-2-yl}benzamide; M+1=646 and 648; prepared according to methods A and B;

4-(4-fluorophenyl)-7-{[{5-[1-hydroxy-1-(trifluoromethyl)propyl]-1,3,4-oxadiazol-2-yl}(isopropyl)amino]methyl}-2H-chromen-2-one; M+1=506; prepared according to method A and D;

7-[({5-[1-hydroxy-1-(trifluoromethyl)propyl]-1,3,4-oxadiazol-2-yl}amino)methyl]-4-(2-methyl-1,3-thiazol-4-yl)-2H-chromen-2-one; M+1=467; prepared according to method C and A;

4-(4-fluorophenyl)-7-[({5-[1-hydroxy-1-(trifluoromethyl)propyl]-1,3,4-oxadiazol-2-yl}amino)methyl]-6-methyl-2H-chromen-2-one; M+1=478; prepared according to method C and A and B;

N-{[4-(4-fluorophenyl)-2-oxo-2H-chromen-7-yl]methyl}-N-{5-[1-hydroxy-1-(trifluoromethyl)propyl]-1,3,4-oxadiazol-2-yl}acetamide; M+1=506; prepared according to method B and A;

4-(4-fluorophenyl)-7-({[5-(1-hydroxy-1-phenylethyl)-1,3,4-oxadiazol-2-yl]amino}methyl)-2H-chromen-2-one; M+1=458; prepared according to method A and B;

4-(4-fluorophenyl)-7-[({5-[2,2,2-trifluoro-1-hydroxy-1-(trifluoromethyl)ethyl]-1,3,4-oxadiazol-2-yl}amino)methyl]-2H-chromen-2-one; M+1=504; prepared according to method A and B;

4-(4-fluorophenyl)-7-[({5-[(1S)-2,2,2-trifluoro-1-hydroxy-1-methylethyl]-1,3,4-oxadiazol-2-yl}amino)methyl]-2H-chromen-2-one; M+1=450; prepared according to method A and B;

4-(4-fluorophenyl)-7-{[{5-[1-hydroxy-1-(trifluoromethyl)propyl]-1,3,4-oxadiazol-2-yl}(methyl)amino]methyl}-2H-chromen-2-one; M+1=478; prepared according to method A and B;

4-(4-fluorophenyl)-7-[({5-[(1R)-2,2,2-trifluoro-1-hydroxy-1-methylethyl]-1,3,4-oxadiazol-2-yl}amino)methyl]-2H-chromen-2-one; M+1=450; prepared according to method A and B;

3-{7-[({5-[1-hydroxy-1-(trifluoromethyl)propyl]-1,3,4-oxadiazol-2-yl}amino)methyl]-2-oxo-2H-chromen-4-yl}benzonitrile; M+1=471;; prepared according to method A and B;

4-(4-fluorophenyl)-7-({[5-(2,2,3,3,3-pentafluoro-1-hydroxy-1-methylpropyl)-1,3,4-oxadiazol-2-yl]amino}methyl)-2H-chromen-2-one; M+1=500; prepared according to method A and B;

4-(4-fluorophenyl)-7-({[5-(1-hydroxycyclopentyl)-1,3,4-oxadiazol-2-yl]amino}methyl)-2H-chromen-2-one; M+1=422; prepared according to method A and B;

(R)-6-fluoro-4-(4-fluorophenyl)-7-[({5-[1-hydroxy-1-(trifluoromethyl)propyl]-1,3,4-oxadiazol-2-yl}amino)methyl]-2H-chromen-2-one; (M+1=464; (R)-isomer in DMSO-d$_6$: 8.57 (t, 1H), 7.68-7.63 (m, 2H), 7.53 (d, 1H), 7.42 (apparent t, 2H), 7.26 (s, 1H), 7.18 (d, 1H), 6.53 (s, 1), 4.55 (d, 2H), 2.15-2.05 (m, 1H), 2.01-1.94 (m, 1H), 0.91 (t, 3H); prepared according to method A and B and separation on CHIRAL PAK AD slow eluting;

(S)-6-fluoro-4-(4-fluorophenyl)-7-[({5-[1-hydroxy-1-(trifluoromethyl)propyl]-1,3,4-oxadiazol-2-yl}amino)methyl]-2H-chromen-2-one; M+1=464; (S)-isomer in acetone-d$_6$: 7.70-7.65 (m, 2H), 7.58-7.52 (m, 2H), 7.39 (apparent t, 2H), 7.23 (d, 1H), 6.42 (s, 1H), 6.10 (br s, 1H), 4.73 (d, 2H), 2.26-2.17 (m, 1H), 2.14-2.03 (m, 1H), 0.97 (t, 3H); prepared according to method A and B and separation on CHIRAL PAK AD fast eluting;

6-chloro-4-(4-fluorophenyl)-7-[({5-[1-hydroxy-1-(trifluoromethyl)propyl]-1,3,4-oxadiazol-2-yl}amino)methyl]-2H-chromen-2-one; M+1=498; prepared according to method A and B;

6-fluoro-4-(4-fluorophenyl)-7-[({5-[1-hydroxy-1-(trifluoromethyl)propyl]-1,3,4-oxadiazol-2-yl}amino)methyl]-2H-chromen-2-one; M+1=482 for the racemate; prepared according to method A and B;

4-(4-fluorophenyl)-7-[({5-[hydroxy(phenyl)methyl]-1,3,4-oxadiazol-2-yl}amino)methyl]-2H-chromen-2-one; M+1=444; prepared according to method A and B;

7-({[5-(1-ethyl-1-hydroxypropyl)-1,3,4-oxadiazol-2-yl]amino}methyl)-6-fluoro-4-(4-fluorophenyl)-2H-chromen-2-one; M+1=442; prepared according to method A and B;

4-(4-fluorophenyl)-7-({[5-(1-hydroxy-1-methylpropyl)-1,3,4-oxadiazol-2-yl]amino}methyl)-2H-chromen-2-one; M+1=410; prepared according to method A and B;

7-({[5-(1-ethylpropyl)-1,3,4-oxadiazol-2-yl]amino}methyl)-4-(4-fluorophenyl)-2H-chromen-2-one; M+1=408; prepared according to method A and B;

4-[3-(difluoromethoxy)phenyl]-7-({[5-(1-ethyl-1-hydroxypropyl)-1,3,4-oxadiazol-2-yl]amino}methyl)-2H-chromen-2-one; M+1=472; prepared according to method A and B;

4-(4-fluorophenyl)-7-[({5-[1-hydroxy-1-(trifluoromethyl)propyl]-1,3,4-oxadiazol-2-yl}amino)methyl]-2H-chromen-2-one; M+1=464 (racemic); prepared according to method A and B;

(+)-4-(4-fluorophenyl)-7-[({5-[1-hydroxy-1-(trifluoromethyl)propyl]-1,3,4-oxadiazol-2-yl}amino)methyl]-2H-chromen-2-one; M+1=464; prepared according to method A and B and separation on CHIRAL PAK AD slow eluting, see example 7;

(−)-4-(4-fluorophenyl)-7-[({5-[1-hydroxy-1-(trifluoromethyl)propyl]-1,3,4-oxadiazol-2-yl}amino)methyl]-2H-chromen-2-one; M+1=464; prepared according to method A and B and separation on CHIRAL PAK AD fast eluting, see example 7;

7-({[5-(1-ethyl-1-hydroxypropyl)-1,3,4-oxadiazol-2-yl]amino}methyl)$_4$-[3-(trifluoromethoxy)phenyl]-2H-chromen-2-one; M+1=490; prepared according to method A and B;

6-chloro-7-({[5-(1-ethyl-1-hydroxypropyl)-1,3,4-oxadiazol-2-yl]amino}methyl)-4-phenyl-2H-chromen-2-one; M+1=440; prepared according to method A and B;

7-({[5-(1-ethyl-1-hydroxypropyl)-1,3,4-oxadiazol-2-yl]
amino}methyl)-4-(3-methylphenyl)-2H-chromen-2-one;
M+1=420; prepared according to method C and B;
7-(1-{[5-(1-ethyl-1-hydroxypropyl)-1,3,4-oxadiazol-2-yl]
amino}ethyl)-4-(4-fluorophenyl)-2H-chromen-2-one;
M+1=438; prepared according to method A and B;
7-({[5-(1-ethyl-1-fluoropropyl)-1,3,4-oxadiazol-2-yl]
amino}methyl)-4-(4-fluorophenyl)-2H-chromen-2-one;
M+1=426; prepared according to method A and B;
7-{[(5-cyclobutyl-1,3,4-oxadiazol-2-yl)amino]methyl}-4-
(4-fluorophenyl)-2H-chromen-2-one; M+1=392; prepared
according to method A and B;
7-{[(5-cyclopentyl-1,3,4-oxadiazol-2-yl)amino]methyl}-4-
(4-fluorophenyl)-2H-chromen-2-one; M+1=406; prepared
according to method A and B;
7-({[5-(1-ethyl-1-hydroxypropyl)-1,3,4-oxadiazol-2-yl]
amino}methyl)-4-(4-fluorophenyl)chroman-2-one;
M+1=426; prepared according to method A and B;
7-{[[5-(1-ethyl-1-hydroxypropyl)-1,3,4-oxadiazol-2-yl]
(methyl)amino]methyl}-4-(4-fluorophenyl)-2H-
chromen-2-one; M+1=438; prepared according to method
A and B;
7-({[5-(1-ethyl-1-hydroxypropyl)-1,3,4-oxadiazol-2-yl]
amino}methyl)-4-(3-fluorophenyl)-2H-chromen-2-one;
M+1=424; prepared according to method A and B;
4-(2,4-difluorophenyl)-7-({[5-(1-ethyl-1-hydroxypropyl)-1,
3,4-oxadiazol-2-yl]amino}methyl)-2H-chromen-2-one;
M−1=440; prepared according to method A and B;
7-({[5-(1-ethyl-1-hydroxypropyl)-1,3,4-oxadiazol-2-yl]
amino}methyl)-4-(3-methoxyphenyl)-2H-chromen-2-
one; M+1=436; prepared according to method A and B;
7-({[5-(1-ethyl-1-hydroxypropyl)-1,3,4-oxadiazol-2-yl]
amino}methyl)-4-(4-methoxyphenyl)-2H-chromen-2-
one; M+1=436; prepared according to method A and B;
7-({[5-(1-ethyl-1-hydroxypropyl)-1,3,4-oxadiazol-2-yl]
amino}methyl)-4-phenyl-2H-chromen-2-one; M+1=406;
prepared according to method A and B;
7-[({5-[dicyclopropyl(hydroxy)methyl]-1,3,4-oxadiazol-2-
yl}amino)methyl]-4-(4-fluorophenyl)-2H-chromen-2-
one; M+1=448; prepared according to method A and B;
7-({[5-(1-ethyl-1-hydroxypropyl)-1,3,4-oxadiazol-2-yl]
amino}methyl)-4-(4-fluorophenyl)-2H-chromen-2-one;
M+1=424; prepared according to method A and B;
N-[5-(1-ethyl-1-hydroxypropyl)-1,3,4-oxadiazol-2-yl]-N-{
[4-(4-fluorophenyl)-2-oxo-2H-chromen-7-yl]
methyl}acetamide; M+1=466; prepared according to
method A;
7-({[5-(1-ethyl-1-hydroxypropyl)-1,3,4-thiadiazol-2-yl]
amino}methyl)-4-(4-fluorophenyl)-2H-chromen-2-one;
M+1=440; prepared according to method B and D;
7-{[(5-tert-butyl-1,3,4-thiadiazol-2-yl)amino]methyl}-4-(4-
fluorophenyl)-2H-chromen-2-one; M−1=408; prepared
according to method B;
7-({5-[dicyclopropyl(hydroxy)methyl]-1,3,4-thiadiazol-2-
yl}thio)-4-pyridin-3-yl-2H-chromen-2-one; M+1=450;
prepared according to method C and E;
7-({5-[dicyclopropyl(hydroxy)methyl]-1,3,4-thiadiazol-2-
yl}thio)-4-(4-fluorophenyl)-2H-chromen-2-one;
M+1=467; prepared according to method C and E;
7-{[5-(1-ethyl-1-hydroxypropyl)-1,3,4-thiadiazol-2-yl]
thio}-4-(4-fluorophenyl)-2H-chromen-2-one; M+1=443;
prepared according to method C and E; and the pharmaceutically acceptable salts, esters and solvates thereof,
where appropriate.

The compounds of this invention, including compounds referenced as those of "Formula I," "Formula Ia," "Formula Ib," "Formula Ic" or any other generic structural formulas used herein to describe the compounds of this invention, are intended to encompass compounds falling within the scope of each of these structural formulas including pharmaceutically acceptable salts, esters and solvates thereof where such salts, esters and solvates are possible. The term "pharmaceutically acceptable salts" refers to salts prepared from pharmaceutically acceptable non-toxic bases, such as for example, a sodium salt which could be prepared using NaOH. Pharmaceutically acceptable esters of available hydroxy or carboxylic acid groups can optionally be formed as well. Examples of pharmaceutically acceptable esters include, but are not limited to, —$C_{1-4}$ alkyl and —$C_{1-4}$ alkyl substituted with phenyl-, dimethylamino- and acetylamino.

Some of the compounds described herein contain one or more asymmetric (chiral) centers and may thus exist as racemic mixtures and optical isomers including enantio-enriched mixtures, single enantiomers, diastereomers and mixtures of diastereomers. The present invention is meant to comprehend all such possible enantiomers and diastereomers as well as their racemic and resolved, enantiomerically pure and substantially pure forms, and pharmaceutically acceptable salts thereof. Furthermore, some of the crystalline forms of compounds of the present invention may exist as polymorphs and as such are intended to be included in the present invention. In addition, some of the compounds of the instant invention may form solvates with water or common organic solvents. Such solvates and hydrates are likewise encompassed within the scope of this invention. Some of the compounds described herein contain olefinic double bonds. The invention includes both E and Z geometric isomers.

Compounds of this invention may be separated into their individual diastereoisomers by, e.g., fractional crystallization from suitable solvents, e.g., methylene chloride/hexanes or EtOAc/hexanes, or via chiral chromatography using an optically active stationary phase. Absolute stereochemistry may be determined by X-ray crystallography of crystalline products or crystalline intermediates which are derivatized, if necessary, with a reagent containing a stereogenic center of known configuration. Alternatively, any stereoisomer of a compound of this invention may be obtained by stereospecific synthesis using optically pure starting materials or reagents of known absolute configuration.

As used herein "alkyl" is intended to include both branched- and straight-chain saturated aliphatic hydrocarbon groups having the specified number of carbon atoms, e.g., methyl (Me), ethyl (Et), n-propyl (Pr), n-butyl (Bu), n-pentyl, n-hexyl, and the isomers thereof such as isopropyl (i-Pr), isobutyl (i-Bu), secbutyl (s-Bu), tertbutyl (t-Bu), isopentyl, isohexyl and the like. "Cycloalkyl" means a monocyclic saturated carbocyclic ring, having the specified number of carbon atoms, e.g., 3, 4, 5 or 6 carbon atoms. Examples of cycloalkyl include cyclopropyl, cyclobutyl, cyclopentyl and cyclohexyl.

The term "$C_{2-6}$alkenyl" as used herein, refers to a straight or branched 2-6 carbon chain with at least one carbon-carbon double bond. Examples of alkenyl include, but are not limited to, vinyl (—CH═$CH_2$), allyl, isopropenyl, pentenyl, hexenyl, heptenyl, 1-propenyl, 2-butenyl, 2-methyl-2-butenyl, and the like. The term "$C_{5-7}$ cycloalkenyl" as used herein means a non-aromatic monocyclic ring having from 5 to 7 carbon atoms in the ring with at least one carbon-carbon double bond.

Within the definition of variables above, $R^3$ and $R^4$ can be joined together with the carbon to which they are attached to form a —$C_{5-7}$cycloalkenyl ring wherein there is no double bond at the C-1 position in the ring. The C-1 position is intended to be the ring carbon in the cycloalkenyl ring that is bonded to the core oxadiazolyl or thiadiazolyl ring in the generic structural formulas depicted herein. In this situation, C-1 is also bonded to $R^2$. This is illustrated below using the example where $R^3$ and $R^4$ are joined together with the carbon to which they are attached to form a 3,4-cyclopentenyl ring, see (a):

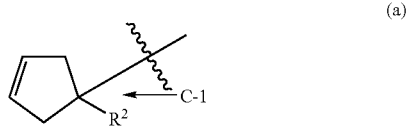

(a)

The term "optionally substituted" means "unsubstituted or substituted," and therefore, the generic structural formulas described herein encompasses compounds containing the specified optional substituent as well as compounds that do not contain the optional substituent. For example, the phrase "—C(O)phenyl optionally substituted with —$C_{1-4}$ alkyl" encompasses unsubstituted —C(O)phenyl and —C(O)phenyl substituted with —$C_{1-4}$ alkyl. Each variable is independently defined each time it occurs within the generic structural formula definitions. For example, when $R^9$ is —$CR^1R^1OH$, $R^1$ is independently selected at each occurrence and each $R^1$ can be the same or different.

Use of the term "substituted" is intended to encompass mono- and poly-substitution on the specified moiety, unless otherwise specified. A mono-substituted moiety has one substituent, while a poly-substituted moiety has more than one substituent wherein each carbon atom, as well as heteroatom such as nitrogen if present, that is available for substitution in the moiety may independently be unsubstituted, mono- or poly-substituted and which results in the creation of a stable structure. For example, "—$C_{1-6}$alkyl optionally substituted with fluoro" includes —$CH_3$, —$CH_2F$, —$CHF_2$ and —$CF_3$.

The terms "halo" or "halogen" are meant to include fluoro, chloro, bromo and iodo, unless otherwise noted. Fluoro and chloro are preferred, and fluoro is most preferred.

Examples of 5-membered aromatic rings within the definitions of A and Z include but are not limited to thienyl, furanyl, oxazolyl, thiazolyl, pyrrolyl, pyrazolyl, imidazolyl, and tetrazolyl, represented by the structural formulas below:

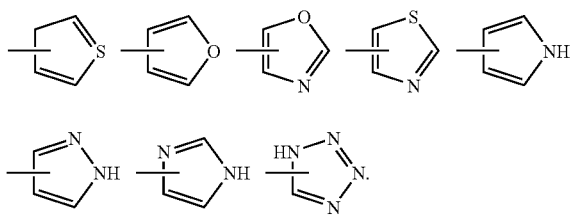

Examples of 6-membered aromatic rings comprised of carbon and one, two or three of —N— within the definition of A and Z include but are not limited to pyridinyl, pyrimidinyl, pyrazinyl and triazinyl represented by the structural formulas below:

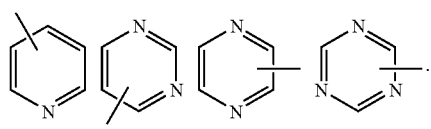

The ability of the compounds of this invention to inhibit biosynthesis of the leukotrienes makes them useful for preventing or reversing the symptoms induced by the leukotrienes in a human subject. This inhibition of the mammalian biosynthesis of leukotrienes indicates that the compounds and pharmaceutical compositions thereof are useful to treat, prevent, or ameliorate atherosclerosis in mammals, and especially in humans. Therefore, the compounds of this invention can be used for the treatment of atherosclerosis comprising administering a therapeutically effective amount of a compound of this invention to a patient in need of such treatment. A further aspect of this invention involves a method for preventing or reducing the risk of developing atherosclerosis, comprising administering a prophylactically effective amount of a compound of this invention to a patient in need of such treatment. Atherosclerosis is characterized by the deposition of atheromatous plaques containing cholesterol and lipids on the innermost layer of the walls of large and medium-sized arteries. Atherosclerosis encompasses vascular diseases and conditions that are recognized and understood by physicians practicing in the relevant fields of medicine. Atherosclerotic cardiovascular disease including restenosis following revascularization procedures, coronary heart disease (also known as coronary artery disease or ischemic heart disease), cerebrovascular disease including multi-infarct dementia, and peripheral vessel disease including erectile dysfunction, are all clinical manifestations of atherosclerosis and are therefore encompassed by the terms "atherosclerosis" and "atherosclerotic disease."

A compound of the instant invention may be administered to prevent or reduce the risk of occurrence, or recurrence where the potential exists, of a coronary heart disease (CHD) event, a cerebrovascular event, and/or intermittent claudication. Coronary heart disease events are intended to include CHD death, myocardial infarction (i.e., a heart attack), and coronary revascularization procedures. Cerebrovascular events are intended to include ischemic or hemorrhagic stroke (also known as cerebrovascular accidents) and transient ischemic attacks. Intermittent claudication is a clinical manifestation of peripheral vessel disease. The term "atherosclerotic disease event" as used herein is intended to encompass coronary heart disease events, cerebrovascular events, and intermittent claudication. It is intended that persons who have previously experienced one or more non-fatal atherosclerotic disease events are those for whom the potential for recurrence of such an event exists.

Accordingly, the instant invention also provides a method for preventing or reducing the risk of a first or subsequent occurrence of an atherosclerotic disease event comprising the administration of a prophylactically effective amount of a compound of this invention to a patient at risk for such an event. The patient may already have atherosclerotic disease at the time of administration, or may be at risk for developing it.

The method of this invention serves to prevent or slow new atherosclerotic lesion or plaque formation, and to prevent or slow progression of existing lesions or plaques, as well as to cause regression of existing lesions or plaques. Accordingly, one aspect of this invention involves a method for halting or slowing the progression of atherosclerosis, including halting or slowing atherosclerotic plaque progression, comprising administering a therapeutically effective amount of a compound of this invention to a patient in need of such treatment. This method also includes halting or slowing progression of atherosclerotic plaques existing at the time the instant treatment is begun (i.e., "existing atherosclerotic plaques"), as well as halting or slowing formation of new atherosclerotic plaques in patients with atherosclerosis.

Another aspect of this invention involves a method for regression of atherosclerosis, including regression of atherosclerotic plaques existing at the time the instant treatment is begun, comprising administering a therapeutically effective amount of a compound of this invention to a patient in need of such treatment.

Another aspect of this invention involves a method for preventing or reducing the risk of atherosclerotic plaque rupture comprising administering a prophylactically effective amount of a compound of this invention to a patient in need of such treatment. Another aspect of this invention involves a method for treating, preventing, or ameliorating angina and/or myocardial ischemia, comprising administering a therapeutically or prophylactically effective amount, as appropriate, of a compound of this invention to a patient in need of such treatment.

Additionally, the activity of the instant compounds as leukotriene biosynthesis inhibitors makes them useful for treating, preventing, or ameliorating: 1) pulmonary disorders including diseases such as asthma, chronic bronchitis, and related obstructive airway diseases, 2) allergies and allergic reactions such as allergic rhinitis, contact dermatitis, allergic conjunctivitis, and the like, 3) inflammation such as arthritis or inflammatory bowel disease, 4) pain, 5) skin disorders such as atopic eczema, and the like, 6) cardiovascular disorders such hypertension, platelet aggregation and the like, 7) renal insufficiency arising from ischaemia induced by immunological or chemical (cyclosporin) etiology and 8) migraine or cluster headache, 9) ocular conditions such as uveitis, 10) hepatitis resulting from chemical, immunological or infectious stimuli, 11) trauma or shock states such as burn injuries, endotoxemia and the like, 12) allograft rejection, 13) prevention of side effects associated with therapeutic administration of cytokines such as Interleukin II and tumor necrosis factor, 14) chronic lung diseases such as cystic fibrosis, bronchitis and other small- and large-airway diseases, 15) cholecystitis, 16) multiple sclerosis, 17) proliferation of myoblastic leukemia cells and 18) acne.

Thus, the compounds of the present invention may also be used to treat or prevent mammalian (especially, human) disease states such as erosive gastritis; erosive esophagitis; diarrhea; cerebral spasm; premature labor; spontaneous abortion; dysmenorrhea; ischemia; noxious agent-induced damage or necrosis of hepatic, pancreatic, renal, or myocardial tissue; liver parenchymal damage caused by hepatoxic agents such as $CCl_4$ and D-galactosamine; ischemic renal failure; disease-induced hepatic damage; bile salt induced pancreatic or gastric damage; trauma- or stress-induced cell damage; and glycerol-induced renal failure. Leukotriene biosynthesis inhibitors also act as inhibitors of tumor metastasis and exhibit cytoprotective action.

The cytoprotective activity of a compound may be observed in both animals and man by noting the increased resistance of the gastrointestinal mucosa to the noxious effects of strong irritants, for example, the ulcerogenic effects of aspirin or indomethacin. In addition to lessening the effect of non-steroidal anti-inflammatory drugs on the gastrointestinal tract, animal studies show that cytoprotective compounds will prevent gastric lesions induced by oral administration of strong acids, strong bases, ethanol, hypertonic saline solutions, and the like. Two assays can be used to measure cytoprotective ability. These assays are: (A) an ethanol-induced lesion assay and (B) an indomethacin-induced ulcer assay and are described in EP 140,684. In particular, the compounds of the invention would be useful to reduce the gastric erosion caused by co-administration of a cyclooxygenase-2 selective inhibitor such as rofecoxib (VIOXX®), etoricoxib (ARCOXIA™), celecoxib (CELEBREX®) and valdecoxib (BEXTRA™), and low-dose aspirin.

In addition, the compounds of this invention can also be used for the treatment of chronic obstructive pulmonary disease (COPD). As described in S. Kilfeather, Chest, 2002, vol 121, 197, airway neutrophilia in COPD patients is believed to be a contributing source of inflammation and is associated with airway remodeling. The presence of neutrophils is mediated in part by $LTB_4$, and treatment with the instant compounds could be used to reduce neutrophilic inflammation in patients with COPD.

Furthermore, the compounds of this invention could be used for the treatment of Alzheimer's disease; see Manev, H. and Manev, R., "5-*Lipoxygenase (ALOX5) and FLAP (ALOX5AP) gene polymorphisms as factors in vascular pathology and Alzheimer's disease,*" Medical Hypotheses (2006) 66, p. 501-503.

The term "patient" includes mammals, especially humans, who use the instant active agents for the prevention or treatment of a medical condition. Administering of the drug to the patient includes both self-administration and administration to the patient by another person. The patient may be in need of treatment for an existing disease or medical condition, or may desire prophylactic treatment to prevent or reduce the risk for diseases and medical conditions affected by inhibition of leukotriene biosynthesis.

The term "therapeutically effective amount" is intended to mean that amount of a drug or pharmaceutical agent that will elicit the biological or medical response of a tissue, a system, animal or human that is being sought by a researcher, veterinarian, medical doctor or other clinician. The term "prophylactically effective amount" is intended to mean that amount of a pharmaceutical drug that will prevent or reduce the risk of occurrence of the biological or medical event that is sought to be prevented in a tissue, a system, animal or human by a researcher, veterinarian, medical doctor or other clinician.

The magnitude of prophylactic or therapeutic dose of a compound of this invention will, of course, vary with the nature of the severity of the condition to be treated and with the particular compound and its route of administration. It will also vary according to the age, weight and response of the individual patient. In general, the daily dose range for anti-asthmatic, anti-inflammatory, anti-allergic or anti-atherosclerotic use and generally, uses other than cytoprotection, lie within the range of from about 0.001 mg to about 100 mg per kg body weight of a mammal, preferably 0.01 mg to about 10 mg per kg, and most preferably 0.1 to 1 mg per kg, in single or divided doses. On the other hand, it may be necessary to use dosages outside these limits in some cases. As examples, the total daily dosage amount may be selected from, but not limited to, 1 mg, 5 mg, 10 mg, 15 mg, 20 mg, 25 mg, 50 mg, 75 mg, 100 mg, 125 mg, 150 mg, 200 mg and 250 mg in single or divided daily doses.

In the case where an oral composition is employed, a suitable dosage range for anti-asthmatic, anti-inflammatory, anti-allergic or anti-atherosclerotic use is, e.g., from about 0.01 mg to about 100 mg of a compound of this invention per kg of body weight per day, preferably from about 0.1 mg to about 10 mg per kg and for cytoprotective use from 0.1 mg to about 100 mg (preferably from about 1 mg to about 100 mg and more preferably from about 10 mg to about 100 mg) of a compound of this invention per kg of body weight per day.

For use where a composition for intravenous administration is employed, a suitable dosage range for anti-asthmatic, anti-inflammatory, anti-atherosclerotic or anti-allergic use is from about 0.001 mg to about 25 mg (preferably from 0.01 mg to about 1 mg) of a compound of this invention per kg of body weight per day and for cytoprotective use from about 0.1 mg to about 100 mg (preferably from about 1 mg to about 100 mg and more preferably from about 1 mg to about 10 mg) of a compound of this invention per kg of body weight per day.

For the treatment of diseases of the eye, ophthalmic preparations for ocular administration comprising 0.001-1% by weight solutions or suspensions of the compounds of this invention in an acceptable ophthalmic formulation may be used.

The exact amount of a compound of this invention to be used as a cytoprotective agent will depend on, inter alia, whether it is being administered to heal damaged cells or to avoid future damage, on the nature of the damaged cells (e.g., gastrointestinal ulcerations vs. nephrotic necrosis), and on the nature of the causative agent. An example of the use of a compound of this invention in avoiding future damage would be co-administration of a compound of this invention with an NSAID that might otherwise cause such damage (for example, indomethacin). For such use, the compound of this invention is administered from 30 minutes prior up to 30 minutes after administration of the NSAID. Preferably it is administered prior to or simultaneously with the NSAID, (for example, in a combination dosage form).

The pharmaceutical compositions of the present invention comprise a compound of this invention as an active ingredient and a pharmaceutically acceptable carrier and optionally other therapeutic ingredients. Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. For use in treating or preventing atherosclerosis and related disease events, oral formulation is preferred.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of this invention in suitable propellants, such as fluorocarbons or hydrocarbons.

Suitable topical formulations of a compound of this invention include transdermal devices, aerosols, creams, ointments, lotions, dusting powders, and the like.

In practical use, the compounds of this invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of this invention may also be administered by controlled release means and/or delivery devices such as those described in U.S. Pat. Nos. 3,845,770; 3,916,899; 3,536,809; 3,598,123; 3,630,200; 4,008,719; and 5,366,738 the disclosures of which are hereby incorporated herein by reference.

Pharmaceutical compositions of the present invention suitable for oral administration may be presented as discrete units such as capsules, cachets or tablets, each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet, cachet or capsule contains from about 1 mg to about 500 mg of the active ingredient. The following are examples of representative pharmaceutical dosage forms for the compounds of this invention:

| Injectable Suspension (I.M.) | mg/ml |
|---|---|
| Compound of Formula Ia | 10 |
| Methylcellulose | 5.0 |
| Tween 80 | 0.5 |
| Benzyl alcohol | 9.0 |
| Benzalkonium chloride | 1.0 |
| Water for injection to a total volume of 1 ml | |

| Tablet | mg/tablet |
| --- | --- |
| Compound of Formula Ia | 25 |
| Microcrystalline Cellulose | 415 |
| Providone | 14.0 |
| Pregelatinized Starch | 43.5 |
| Magnesium Stearate | 2.5 |
| | 500 |

| Capsule | mg/capsule |
| --- | --- |
| Compound of Formula Ia | 25 |
| Lactose Powder | 573.5 |
| Magnesium Stearate | 1.5 |
| | 600 |

| Aerosol | Per canister |
| --- | --- |
| Compound of Formula Ia | 24 mg |
| Lecithin, NF Liquid Concentrate | 1.2 mg |
| Trichlorofluoromethane, NF | 4.025 gm |
| Dichlorodifluoromethane, NF | 12.15 gm |

The instant invention also encompasses a process for preparing a pharmaceutical composition comprising combining a compound of this invention with a pharmaceutically acceptable carrier. Also encompassed is the pharmaceutical composition which is made by combining a compound of this invention with a pharmaceutically acceptable carrier.

A therapeutically effective amount of a compound of this invention can be used for the preparation of a medicament useful for treating or preventing any of the medical conditions described herein, in dosage amounts described herein. For example, a compound of this invention can be used for the preparation of a medicament useful for the treatment of asthma, allergies and allergic conditions, inflammation, COPD or erosive gastritis. Additionally, the medicament may be useful for preventing or reducing the risk of developing atherosclerotic disease, halting or slowing the progression of atherosclerotic disease once it has become clinically manifest, and preventing or reducing the risk of a first or subsequent occurrence of an atherosclerotic disease event. The medicament comprised of a compound of this invention may also be prepared with one or more additional active agents, such as those described below.

One or more additional active agents may be used in combination with the compounds of this invention in a single dosage formulation, or the active agents of the combination may be administered to the patient in separate dosage formulations, which allows for concurrent or sequential administration of the active agents.

In addition to the compounds of this invention, the pharmaceutical compositions of the present invention can also contain other active agents (i.e., ingredients), such as cyclooxygenase inhibitors, non-steroidal anti-inflammatory drugs (NSAIDs), peripheral analgesic agents such as zomepirac diflunisal and the like. The weight ratio of the compound of this invention to the second active ingredient may be varied and will depend upon the effective dose of each ingredient. Generally, an effective dose of each will be used. Thus, for example, when a compound of this invention is combined with an NSAID the weight ratio of the compound of said compound to the NSAID will generally range from about 1000:1 to about 1:1000, preferably about 200:1 to about 1:200. Combinations of a compound of this invention and other active ingredients will generally also be within the aforementioned range, but in each case, an effective dose of each active ingredient should be used.

NSAIDs can be characterized into five groups: (1) propionic acid derivatives; (2) acetic acid derivatives; (3) fenamic acid derivatives; (4) oxicams; and (5) biphenylcarboxylic acid derivatives; or a pharmaceutically acceptable salt thereof.

The propionic acid derivatives which may be used comprise: alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, prano-profen, suprofen, tiaprofenic acid, and tioxaprofen. Structurally related propionic acid derivatives having similar analgesic and anti-inflammatory properties are also intended to be included in this group. Thus, "propionic acid derivatives" as defined herein are non-narcotic analgesics/non-steroidal anti-inflammatory drugs having a free —CH(CH$_3$)COOH or —CH$_2$CH$_2$COOH group (which optionally can be in the form of a pharmaceutically acceptable salt group, e.g., —CH(CH$_3$) COO$^-$Na$^+$ or —CH$_2$CH$_2$COO$^-$Na$^+$), typically attached directly or via a carbonyl function to a ring system, preferably to an aromatic ring system.

The acetic acid derivatives which may be used comprise: indomethacin, which is a preferred NSAID, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac. Structurally related acetic acid derivatives having similar analgesic and anti-inflammatory properties are also intended to be encompassed by this group. Thus, "acetic acid derivatives" as defined herein are non-narcotic analgesics/non-steroidal anti-inflammatory drugs having a free —CH$_2$COOH group (which optionally can be in the form of a pharmaceutically acceptable salt group, e.g., —CH$_2$COO$^-$Na$^+$), typically attached directly to a ring system, preferably to an aromatic or heteroaromatic ring system.

The fenamic acid derivatives which may be used comprise: flufenamic acid, meclofenamic acid, mefenamic acid, niflumic acid and tolfenamic acid. Structurally related fenamic acid derivatives having similar analgesic and anti-inflammatory properties are also intended to be encompassed by this group. Thus, "fenamic acid derivatives" as defined herein are non-narcotic analgesics/non-steroidal anti-inflammatory drugs which contain the basic structure:

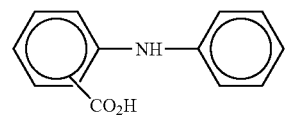

which can bear a variety of substituents and in which the free —COOH group can be in the form of a pharmaceutically acceptable salt group, e.g., —COO$^-$Na$^+$.

The biphenylcarboxylic acid derivatives which can be used comprise: diflunisal and flufenisal. Structurally related biphenyl-carboxylic acid derivatives having similar analgesic and anti-inflammatory properties are also intended to be encompassed by this group. Thus, "biphenylcarboxylic acid derivatives" as defined herein are non-narcotic analgesics/non-steroidal anti-inflammatory drugs which contain the basic structure:

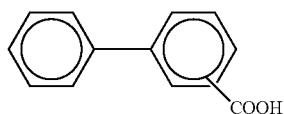

which can bear a variety of substituents and in which the free —COOH group can be in the form of a pharmaceutically acceptable salt group, e.g., —COO$^-$Na$^+$.

The oxicams which can be used in the present invention comprise: isoxicam, piroxicam, sudoxicam and tenoxican. Structurally related oxicams having similar analgesic and anti-inflammatory properties are also intended to be encompassed by this group. Thus, "oxicams" as defined herein are non-narcotic analgesics/non-steroidal anti-inflammatory drugs which have the general formula:

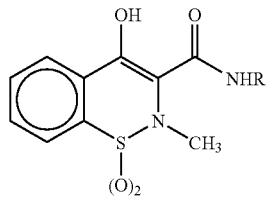

wherein R is an aryl or heteroaryl ring system.

The following NSAIDs may also be used: amfenac sodium, aminoprofen, anitrazafen, antrafenine, auranofin, bendazac lysinate, benzydanine, beprozin, broperamole, bufezolac, cinmetacin, ciproquazone, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclorac, fendosal, fenflumizole, feprazone, floctafenine, flunixin, flunoxaprofen, fluproquazone, fopirtoline, fosfosal, furcloprofen, glucametacin, guaimesal, ibuproxam, isofezolac, isonixim, isoprofen, isoxicam, lefetamine HCl, leflunomide, lofemizole, lonazolac calcium, lotifazole, loxoprofen, lysin clonixinate, meclofenamate sodium, meseclazone, nabumetone, nictindole, nimesulide, orpanoxin, oxametacin, oxapadol, perisoxal citrate, pimeprofen, pimetacin, piproxen, pirazolac, pirfenidone, proglumetacin maleate, proquazone, pyridoxiprofen, sudoxicam, talmetacin, talniflumate, tenoxicam, thiazolinobutazone, thielavin B, tiaramide HCl, tiflamizole, timegadine, tolpadol, tryptamid, and ufenamate. The following NSAIDs, designated by company code number (see e.g., Pharmaprojects), may also be used: 480156S, AA861, AD1590, AFP802, AFP860, AI77B, AP504, AU8001, BPPC, BW540C, CHINOIN 127, CN100, EB382, EL508, F1044, GV3658, ITF182, KCNTEI6090, KME4, LA2851, MR714, MR897, MY309, ONO3144, PR823, PV102, PV108, R830, RS2131, SCR152, SH440, SIR133, SPAS510, SQ27239, ST281, SY6001, TA60, TAI-901 (4-benzoyl-1-indancarboxylic acid), TVX2706, U60257, UR2301, and WY41770.

Finally, NSAIDs which may also be used include the salicylates, specifically acetyl salicylic acid and the phenylbutazones, and pharmaceutically acceptable salts thereof.

In addition to indomethacin, other preferred NSAIDs are acetyl salicylic acid, diclofenac, fenbufen, fenoprofen, flurbiprofen, ibuprofen, ketoprofen, naproxen, phenylbutazone, piroxicam, sulindac, and tolmetin. Pharmaceutical compositions comprising compounds of this invention may also contain inhibitors of the biosynthesis of the leukotrienes such as are disclosed in EP 138,481 (Apr. 24, 1985), EP 115,394 (Aug. 8, 1984), EP 136,893 (Apr. 10, 1985), and EP 140,709 (May 8, 1985), which are hereby incorporated herein by reference.

The compounds of this invention may also be used in combination with leukotriene antagonists such as those disclosed in EP 106,565 (Apr. 25, 1984) and EP 104,885 (Apr. 4, 1984) which are hereby incorporated herein by reference and others known in the art such as those disclosed in EP Application Nos. 56,172 (Jul. 21, 1982) and 61,800 (Jun. 10, 1982); and in U.K. Patent Specification No. 2,058,785 (Apr. 15, 1981), which are hereby incorporated herein by reference.

Pharmaceutical compositions comprising compounds of this invention may also contain as the second active ingredient, prostaglandin antagonists such as those disclosed in EP 11,067 (May 28, 1980) or thromboxane antagonists such as those disclosed in U.S. Pat. No. 4,237,160. They may also contain histidine decarboxylase inhibitors such as α-fluoromethylhistidine, described in U.S. Pat. No. 4,325,961. The compounds of this invention may also be advantageously combined with an $H_1$ or $H_2$-receptor antagonist, such as for instance acetamazole, aminothiadiazoles disclosed in EP 40,696 (Dec. 2, 1981), benadryl, cimetidine, famotidine, framamine, histadyl, phenergan, ranitidine, terfenadine and like compounds, such as those disclosed in U.S. Pat. Nos. 4,283,408; 4,362,736; and 4,394,508. The pharmaceutical compositions may also contain a $K^+/H^+$ ATPase inhibitor such as omeprazole, disclosed in U.S. Pat. No. 4,255,431, and the like. Compounds of this invention may also be usefully combined with most cell stabilizing agents, such as 1,3-bis(2-carboxychromon-5-yloxy)-2-hydroxypropane and related compounds described in British Patent Specifications 1,144,905 and 1,144,906. Another useful pharmaceutical composition comprises compounds of this invention in combination with serotonin antagonists such as methysergide, the serotonin antagonists described in Nature, 316, 126-131 (1985), and the like. Each of the references referred to in this paragraph is hereby incorporated herein by reference.

Other advantageous pharmaceutical compositions comprise the compounds of this invention in combination with anti-cholinergics such as ipratropium bromide, bronchodilators such as the beta agonist salbutamol, metaproterenol, terbutaline, fenoterol and the like, and the anti-asthmatic drugs theophylline, choline theophyllinate and enprofylline, the calcium antagonists nifedipine, diltiazem, nitrendipine, verapamil, nimodipine, felodipine, etc., and the corticosteroids, hydrocortisone, methylprednisolone, betamethasone, dexamethasone, beclomethasone, and the like.

Furthermore, additional active agents such as anti-atherosclerotic agents may be used in combination with the compounds of this invention. The additional active agent or agents can be lipid altering compounds such as HMG-CoA reductase inhibitors, or agents having other pharmaceutical activities, or agents that have both lipid-altering effects and other pharmaceutical activities. Examples of HMG-CoA reductase inhibitors useful for this purpose include statins in their lactonized or dihydroxy open acid forms and pharmaceutically acceptable salts and esters thereof, including but not limited to lovastatin (MEVACOR®; see U.S. Pat. No. 4,342,767); simvastatin (ZOCOR®; see U.S. Pat. No. 4,444,784); dihydroxy open-acid simvastatin, particularly the ammonium or calcium salts thereof; pravastatin, particularly the sodium salt thereof (PRAVACHOL®; see U.S. Pat. No. 4,346,227); fluvastatin particularly the sodium salt thereof (LESCOL®; see U.S. Pat. No. 5,354,772); atorvastatin, particularly the calcium salt thereof (LIPITOR®; see U.S. Pat. No. 5,273,995); nisvastatin also referred to as NK-104 (see PCT international publication number WO 97/23200); and rosuvastatin (CRESTOR®; see U.S. Pat. No. 5,260,440). Additional active agents which may be employed in combination with a compound of this invention include but are not limited to HMG-CoA synthase inhibitors; cholesterol absorption inhibitors such as ezetimibe (ZETIA®) which is 1-(4-fluorophenyl)-3(R)-[3(S)-(4-fluorophenyl)-3-hydroxypropyl)]-4(S)-(4-hydroxyphenyl)-2-azetidinone, described in U.S. Pat. Nos. Re. 37721 and 5,846,966; cholesterol ester transfer protein (CETP) inhibitors, for example JTT-705 (Japan Tobacco Company) and torcetrapib (Pfizer); squalene epoxidase inhibitors; squalene synthetase inhibitors (also known as squalene synthase inhibitors); acyl-coenzyme A: cholesterol acyltransferase (ACAT) inhibitors including selective inhibitors of ACAT-1 or ACAT-2 as well as dual inhibitors of ACAT1 and -2; microsomal triglyceride transfer protein (MTP) inhibitors; probucol; niacin; bile acid sequestrants; LDL (low density lipoprotein) receptor inducers; platelet aggregation inhibitors, for example glycoprotein IIb/IIIa fibrinogen receptor antagonists and aspirin; human peroxisome proliferator activated receptor gamma (PPARγ) agonists including the compounds commonly referred to as glitazones for example troglitazone, pioglitazone and rosiglitazone and, including those compounds included within the structural class known as thiazolidinediones as well as those PPARγ agonists outside the thiazolidinedione structural class; PPARα agonists such as clofibrate, fenofibrate including micronized fenofibrate, and gemfibrozil; PPAR dual α/γ agonists such as muraglitazar; vitamin $B_6$ (also known as pyridoxine) and the pharmaceutically acceptable salts thereof such as the HCl salt; vitamin $B_{12}$ (also known as cyancobalamin); folic acid or a pharmaceutically acceptable salt or ester thereof such as the sodium salt and the methylglucamine salt; anti-oxidant vitamins such as vitamin C and E and beta carotene; beta-blockers; angiotensin II antagonists such as losartan; angiotensin converting enzyme inhibitors such as enalapril and captopril; calcium channel blockers such as nifedipine and diltiazam; endothelian antagonists; agents that enhance ABC1 gene expression; FXR and LXR ligands including both inhibitors and agonists; bisphosphonate compounds such as alendronate sodium; and cyclooxygenase-2 inhibitors such as rofecoxib and celecoxib.

Compounds of this invention can be tested using the following assays to determine their mammalian leukotriene biosynthesis inhibiting activity. Representative tested compounds of this invention were shown to be inhibitors of leukotriene biosynthesis, with most having an $IC_{50}$ less than or equal to 4 μM in the Human 5-Lipoxygenase Enzyme Assay, described below, with preferred compounds tested in this assay having an $IC_{50}$ less than or equal to 0.100 μM. The representative tested compounds were also shown to have activity as 5-LO inhibitors in the 5-Lipoxygenase Human Whole Blood Assay, described below, with most having an $IC_{50}$ less than or equal to 4 μM, and preferred compounds having an $IC_{50}$ of less than or equal to 0.500 μM.

Human 5-Lipoxygenase Enzyme Assay

The activity of 5-lipoxygenase was measured using a spectrophotometric assay and recombinant human 5-lipoxygenase as a source of enzyme. Human 5-lipoxygenase was purified from Sf9 cells infected with the recombinant baculovirus rvH5LO (8-1) containing the coding sequence for human 5-lipoxygenase as described by Percival et al., (Eur. J. Biochem 210, 109-117, 1992). The enzymatic activity was measured using a spectrophotometric assay from the optimal rate of conjugated diene formation (absorbance at 238 nm) using the procedure described in Riendeau et al. (Biochem. Pharmacol. 38, 2313-2321, 1989) with minor modifications. The incubation mixture contained 25 mM potassium phosphate, pH 7.5, 0.1 mM EDTA, 0.3 mM $CaCl_2$, 24 μg/ml phosphatidylcholine, 0.1 mM ATP, 0.5 mM DTT, 20 μM arachidonic acid (2 μl from a 100-fold solution in ethanol), inhibitor (2 μl aliquot from a 100-fold solution in DMSO) and an aliquot of purified 5-lipoxygenase. Reactions were initiated by the addition of the purified 5-lipoxygenase and the rate of conjugated diene production was followed for 5 minutes at room temperature. The reaction was performed in a Costar UV plate (Cat. # 3635) and the absorbance changes at 238 nm were recorded with a Molecular Devices UV/VIS 96 well spectrophotometer (Spectra Max 190) using SOFTmax PRO software. Enzymatic activity was calculated from the optimal rate of the reaction by a linear fit of the increase in absorbance at 238 nm over 36 seconds. When the rate of diene formation is low (<0.01 Absorbance Unit/min) the linear fit is performed over 180 seconds. The results are expressed as percentage of inhibition of the reaction rate relative to controls (typically between 0.001-0.005 Absorbance Unit/min) containing the DMSO vehicle.

5-Lipoxygenase Human Whole Blood Assay

Fresh blood was collected in heparinized tubes by venipuncture from consenting volunteers. These volunteers have no apparent inflammatory conditions and have not taken any nonsteroidal anti-inflammatory drugs for at least 4 days prior to blood collection. Plasma was separated from the blood of each individual volunteer by centrifuging approximately 10 mls of blood. A 50 mM stock solution of the calcium ionophore A23187 (Sigma, St Louis, Mo., USA) in DMSO was diluted 40 fold with each volunteer's plasma to obtain a 1.25 mM working solution. A 250 μl aliquot of each blood was pre-incubated with either 0.5 μl of vehicle (DMSO) or test compounds in DMSO at 37° C. for 15 minutes. This was followed with the addition of 5 μl of either plasma or the 1.25 mM working solution (for each experiment, the blood and plasma was from the same volunteer) resulting in a final concentration of 25 µM of A23187. The blood mixture was incubated at 37° C. for 30 minutes then centrifuged at 1500 g at 4° C. for 10 minutes. The supernatant plasma was collected from all samples and stored at 4° C. All supernatant plasma samples were tested for the production of leukotriene $B_4$ ($LTB_4$) using the $LTB_4$ enzyme immunosorbent assay (EIA) kit from Assay Designs (Ann Arbor, Mich., USA) according to the manufacturer's instructions.

Compounds of this invention may be prepared employing general synthetic procedures known in the art, including methods described in U.S. Pat. No. 5,552,437 and PCT publication WO2004/108720, published Dec. 16, 2004, both publications herein incorporated by reference in their entirety. The synthetic routes outlined in the following methods, reaction schemes and Examples are provided for illustrative purposes. Groups designated "R" in the general schemes as well as solvents, temperatures and others reaction conditions may be selected or modified by one of ordinary skill in the art. Functional groups can be either protected or converted to other functional groups. For example, amino groups can be acylated with an acyl chloride or and anhydride with a mild base such as $K_2CO_3$ or nitrogen base. Esters can be converted to tertiary alcohols with a Grignard reagent or an alkyl lithium reagents.

Some abbreviations used herein include: Ac=acyl; AIBN=2,2'-azobisisobutyronitrile; BuLi is n-butyllithium; CAN=cerium ammonium nitrate; DAST=diethylaminosulfur trifluoride; DBU=1,8-diazabicyclo[5.4.0]undec-7-ene; DCC=1,3-dicyclohexylcarbodiimide; DCM=dichloromethane; DME=ethylene glycol dimethyl ether; DMF=N,N-dimethylformamide; DMSO=dimethyl sulfoxide; EtOH=ethanol; $Et_2O$=diethyl ether; $Et_3N$=triethylamine; EtOAc=ethyl acetate; h=hours; HOAc=acetic acid; KHMDS=potassium bis(trimethylsilyl) amide; LAH=lithium aluminum hydride; LDA=lithium diisopropylamide; m-CPBA=3-chloroperoxybenzoic acid; MeOH=methanol; NBS=N-bromosuccinimide; NMO=4-methylmorpholine N-oxide; NMP=1-methyl-2-pyrrolidinone; OTf=trifluoromethanesulfonate=triflate; O-THP=O-tetrahydropyran-2-yl; PPTS=pyridinium p-toluenesulfonate; rt=room temperature; TBAF=tetrabutylammonium fluoride; $Tf_2O$=triflic anhydride; TFA=trifluoro acetic acid; THF=tetrahydrofuran; TMSCN=trimethylsilyl cyanide.

Oxadiazoles can be prepared, for example, according to literature procedures and references cited therein with the appropriate starting material as follows: White, A. D., et. al. *J. Med. Chem.*, (1996) 39, 4382; Futaki, K. Tosa, S., *Chem. Pharm. Bull.* (1960) 8, 908; *Chem. Abstr.* (1966) 64, 3558a.

Thiadiazoles can be prepared, for example, according to literature procedures and references cited therein with the appropriate starting material as follows: Werber, G., Buccheri, F., Marino, M. L., *J. Hetero. Chem.* (1975) 12, 581; Pandey, V. K., et. al., *Ind. J. Chem.* Sect. B (2003) 42, 2583; Shaban, M. A. E., Mostafa, M. A., Nasr, A. Z. *Pharmazia* (2003) 58, 6; Miyamoto, K., et al., *Chem. Pharm. Bull*, (1985) 33, 5126; Yokohama, S., et. al., *Chem. Pharm. Bull.* (1992) 40, 2391; White, A. D. et al. *J. Med. Chem.* (1996) 39, 4382; Bartels-Keith, J. R., Burgess, M. T. Stevenson, J. M., *J. Org. Chem.* (1977) 42, 3725.

METHOD A (see scheme below): Compound 1 is prepared according to procedures described in U.S. Pat. No. 5,552,437 and WO2004/108720. The methyl group is converted to the mono or dibromo 2 with NBS and heating in an inert solvent such as $CCl_4$ in the presence of a radical initiator such as benzoyl peroxide, AIBN or light. The monobromo compound 2 is treated with an excess of NMO at ca. 100° C. in a solvent like dioxane until complete conversion to the aldehyde 8. Alternatively, the dibromo analog of 2 treated with $AgNO_3$ in dioxane-water at reflux for a short time gave the aldehyde 8. The aldehyde 8 is also obtained from the dibromo analog of 2 with a hot solution of $NH_4OAc$ in HOAc (water can be added).

Compound 4 is prepared at rt from a mixture of 2 (monobromo) and 3 in an inert solvent such as DMF in the presence of a weak base such as $K_2CO_3$. The acetyl is removed with a base such as $NH_4OH$ in THF-water to yield compound 5. The free NH is converted to N-alkyls, N-alkyloyls or N-arylolys with alkyl halides, aliphatic acyl halides or aromatic acyl halides through a mild base in an inert solvent such as DCM.

The double bond of coumarin 5 is reduced to the single bond with hydrogen under pressure (40-60 psi) and heating (40-60° C.) with a catalyst such as palladium on charcoal in a suitable solvent for hydrogenation like ethanol. The hydrogenation can be accomplished at any point of any sequence.

METHOD B (see scheme below): The aldehyde 8 and the amine 9 are refluxed together with or without an acid catalyst such as PPTS in a solvent that forms an azeotrope such as toluene to yield the imine 10. This imine is reduced with $NaBH_4$ or the like to the free NH 5 in ethanol or methanol. If $R^2$=OH, the imine 10 is treated with DAST in DCM at −78° C., brought to rt and then poured into a solution of $NaBH_4$ in ethanol to afford the fluorinated analogue 11.

Alternatively, imine 10 is reacted with Grignard reagents between −95 and −78° C. in THF or ether. The mixture is brought to 0° C. and quenched with $NH_4Cl$, to yield 12.

METHOD C (see scheme below): The coumarin 13 is treated with thiol 14 and an inorganic base such as $K_2CO_3$ in DMF or NMP between 80-120° C. to afford compound 15. Alternatively, the thiol 14 is treated with KOH in methanol for a few minutes and the solvent is removed to dryness. To this potassium salt is added the coumarin 13 in NMP and the mixture is heated to 80-120° C. to yield 15. The coumarin 16 is prepared from the palladium catalyzed reaction of compound 13 in MeOH-DMSO (ca. 1:2) under an atmosphere of CO at 60° C. with a base such as triethylamine until completion.

METHOD D (see scheme below): To a −78° C. THF solution of 17 is added BuLi followed by chlorotrimethylsilane. The temperature is raised to −20° C., cooled back to −78° C. and BuLi is added followed by a reagent having a carbonyl group to furnish 18.

METHOD E (see scheme below): A solution of R-(methylthio)(thioxo)acetate 20, where R is alkyl (see: *Z. Chem.* 1977, vol. 17, 366), and hydrazinecarbodithioic acid potassium salt 19 (see: *J. Am. Chem. Soc.* 1983, 105, 2287) in EtOH is heated to reflux overnight. After cooling, the reaction mixture is extracted with $Et_2O$ and the solvent removed. The residue is purified by flash column chromatography on silica gel to give compound 21.

Method A
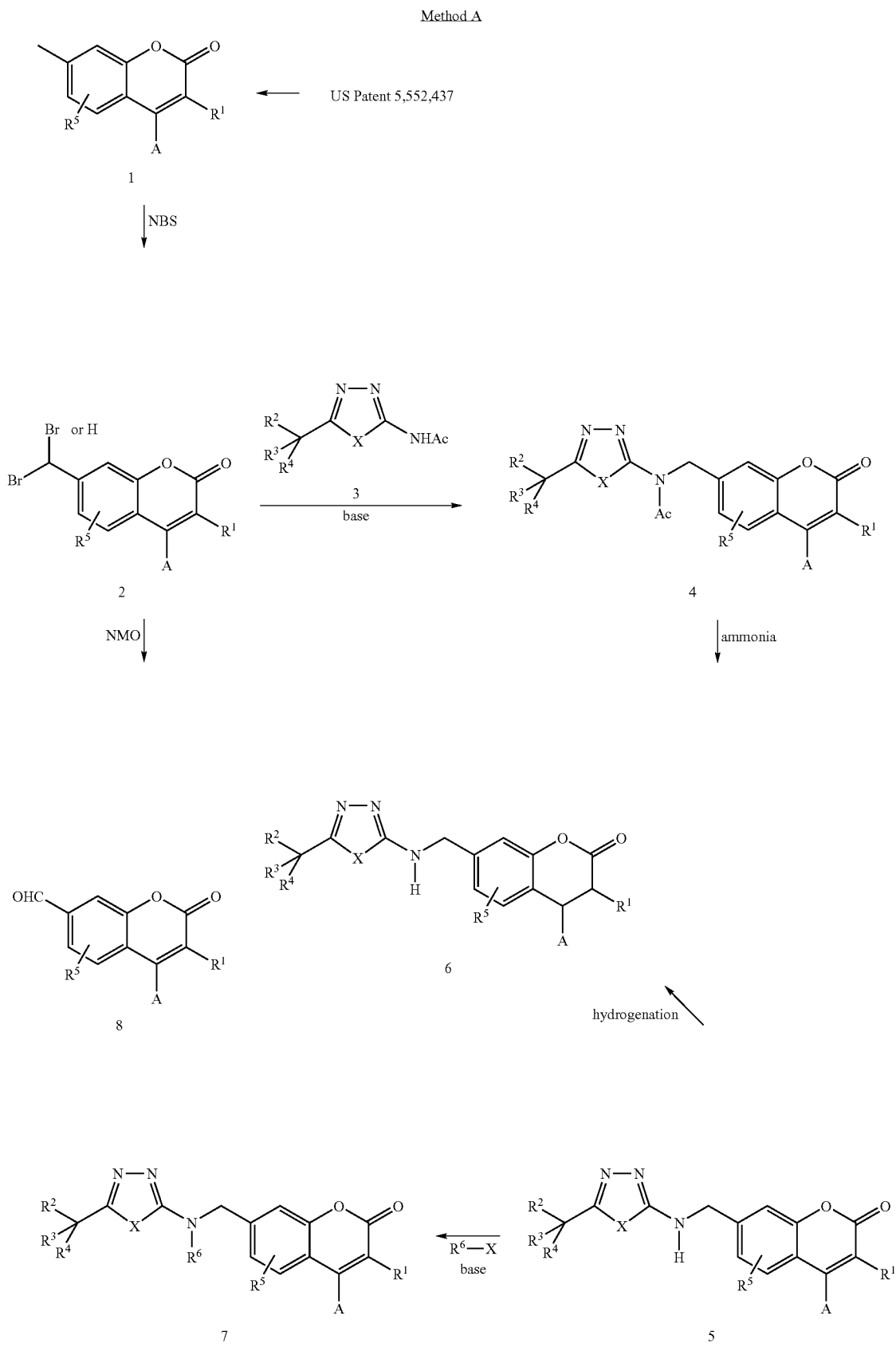

Method B
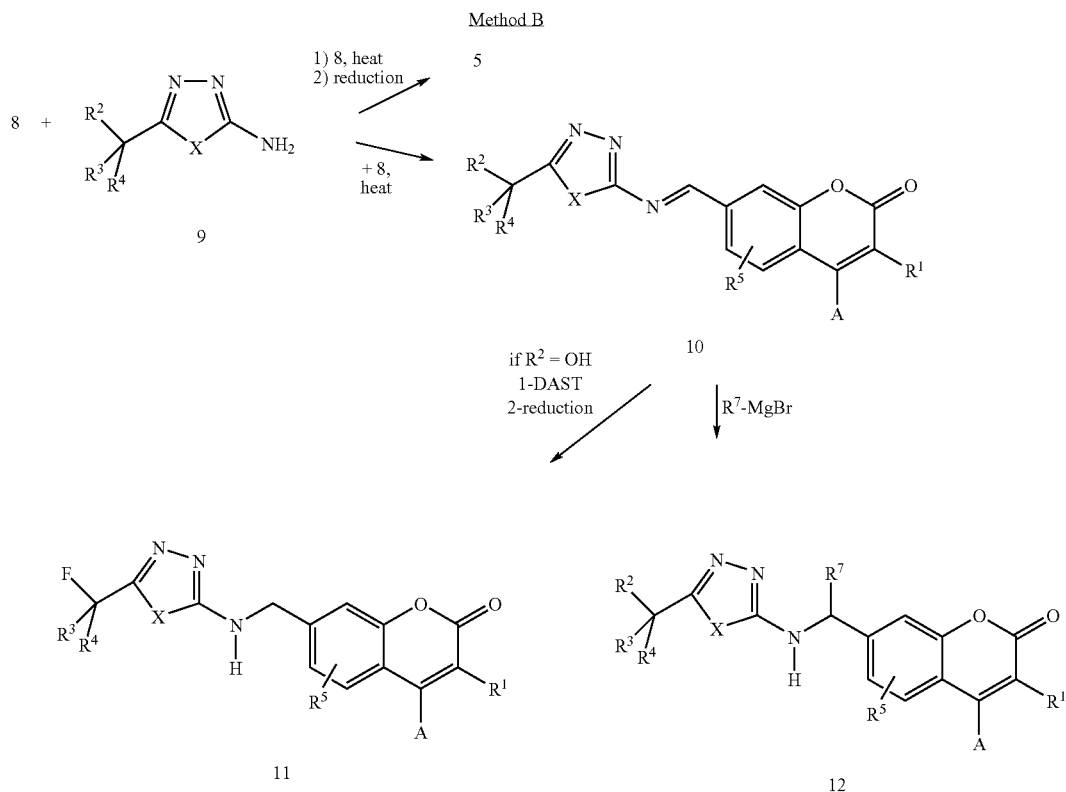
Method C
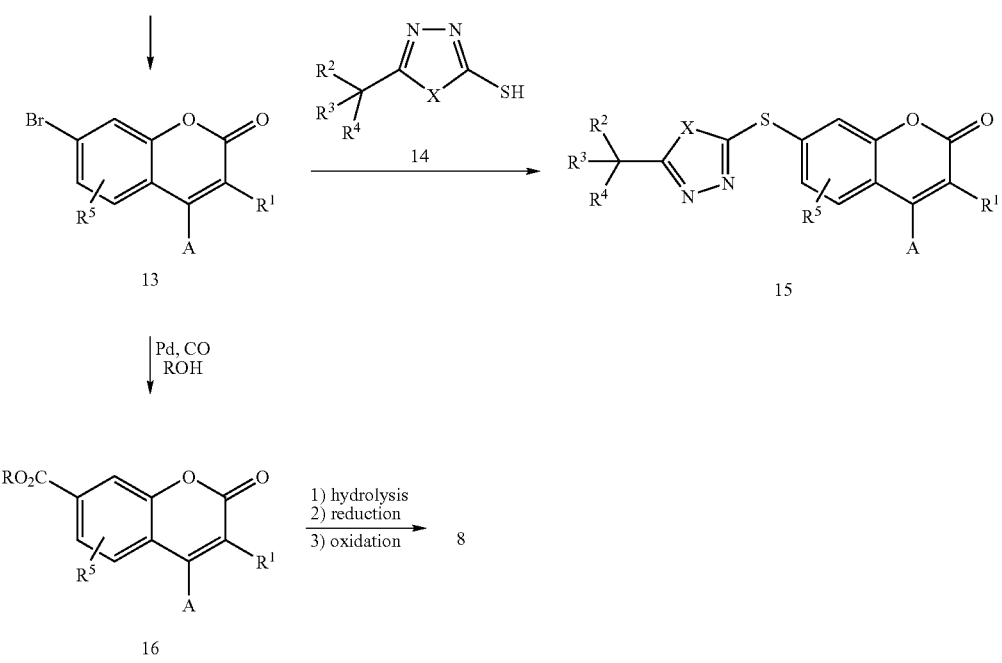

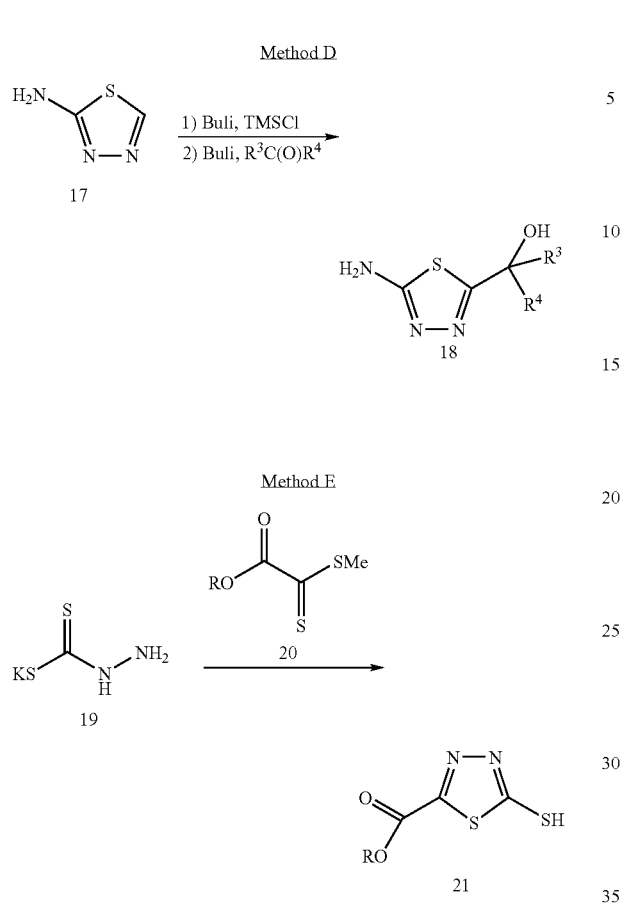

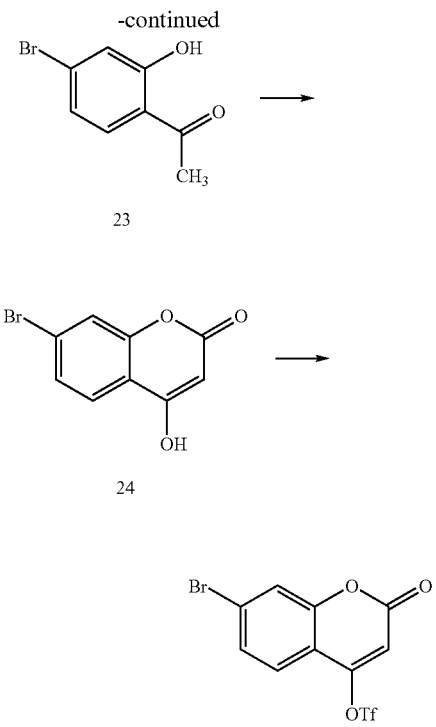

7-Bromo-4-trifluoromethanesulfonyloxycoumarin 25 can be prepared as shown below in Method F. Description of how to make 25 is also found in the procedures described in U.S. Pat. No. 5,552,437 in Scheme I at columns 17-18 (see structure V) therein and in the section titled "Preparation Of Coumarins" starting at column 58 therein. Bromophenol 22 can be acetylated by treating a mixture of 22 and acetyl chloride in the presence of a base such as pyridine in a solvent such as dichloromethane to yield the corresponding acetate which, upon heating neat with a Lewis acid such as aluminum chloride, gives the acyl derivative 23. Reaction of 23 with first an inorganic base such as sodium hydride in an organic solvent such as benzene followed by addition of a carbonate such as diethylcarbonate furnishes the intermediate 24. The intermediate 24 is then transformed using trifluoromethanesulfonic anhydride, in the presence of an amine such as triethylamine, in a neutral solvent such as dichloromethane, to the corresponding triflate 25.

Method F

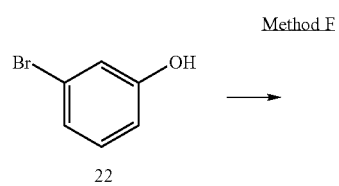

EXAMPLE 1A 7-(Bromomethyl)-4-(4-fluorophenyl)-2H-chromen-2-one

Step 1: 4 Hydroxy-7-methyl-2H-chromen-2-one

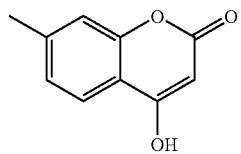

To a 80° C. suspension of NaH (60 g, 1500 mmol, 60%) in toluene was added 1-(2-hydroxy-4-methylphenyl)ethanone (100 g, 666 mmol; also known as 2'-hydroxy-4'-methylacetophenone) in 800 mL of toluene over 1 h. This was followed by the dropwise addition of diethyl carbonate (157 g, 1.3 mol) in 1000 ml of toluene over 1 h. The reaction mixture was left at 80° C. overnight. After cooling to rt, the solution was poured into 1.6 L of HCl (2N). The precipitate formed was filtered, collected and stirred in MeOH (minimum amount). After filtration, the title compound was dried overnight (at 55° C., under high vacuum) to yield the title compound. $^1$H NMR (400 MHz, DMSO-$d_6$): δ 12.45 (1H, s), 7.58 (1H, d), 7.13 (2H, m), 6.53 (1H, s) and 2.39 (3H, s).

Step 2: 4-(4-fluorophenyl)-7-methyl-2H-chromen-2-one

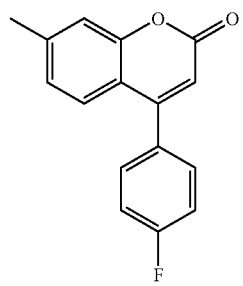

To a –30° C. solution of 4 hydroxy-7-methyl-2H-chromen-2-one (50 g, 284 mmol) and triethylamine (48.8 g, 482 mmol) was added Tf$_2$O (128.1 g, 454 mmol) in 120 ml of CH$_2$Cl$_2$ very slowly (internal Temp. <–30° C.). After 30 min of stirring the solution was brought to 0° C. and quenched with NH$_4$Cl. After extraction with CH$_2$Cl$_2$ the organic phase was washed with H$_2$O (3×), dried over MgSO$_4$ and the solvent removed. The solid obtained was stirred in hexane-ether (9/1). After filtration, the triflate intermediate was dried. $^1$H NMR (400 MHz, acetone-d$_6$): δ 7.68 (1H, d), 7.37 (2H, m), 6.61 (1H, s) and 2.52 (3H, s).

A mixture of the triflate (40 g, 130 mmol), p-fluorophenyl-boronic acid (21.8 g, 156 mmol), Pd(OAc)$_2$ (0.87 g, 3.9 mmol), tricyclohexylphosphine (1.31 g, 4.7 mmol) and potassium fluoride (24.9 g, 428 mmol) in 500 mL of THF was stirred at rt overnight. The mixture was filtered over celite and the solvent removed. The crude product was then purified over a small pad of silica gel using CH$_2$Cl$_2$. The solvent was removed and the resulting solid stirred with CH$_2$Cl$_2$-hexane (1/9). After filtration, the product was dried to yield the title compound. $^1$H NMR (400 MHz, acetone-d$_6$): δ 7.62 (2H, m), 7.39 (3H, m), 7.25 (1H, s), 7.15 (1H, d), 6.29 (1H, s) and 2.45 (3H, s).

Step 3: 7-(bromomethyl)-4-(4-fluorophenyl)-2H-chromen-2-one

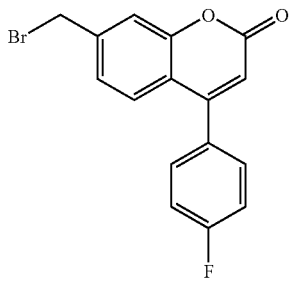

A mixture of 4-(4-fluorophenyl)-7-methyl-2H-chromen-2-one (24.0, 94.3 mmol), NBS (18.5 g, 103.8 mmol) and benzoyl peroxide (1.14 g, 4.72 mmol) in 470 mL of CCl$_4$ was brought to reflux. The solution was left overnight at reflux and then filtered hot. Once cooled to rt the solvent was removed, the compound was dissolved in CH$_2$Cl$_2$ and a purification was done with a small pad of silica gel using hexane-EtOAc (8/2) to (1/1). The solvent was removed and the solid triturated with hexane-EtOAc and filtered to give the title compound. The remaining solvent was removed to give additional compound contaminated with some starting material and dibromo compound. $^1$H NMR (400 MHz, acetone-d$_6$): δ 7.67 (2H, m), 7.55 (1H, s), 7.50 (1H, d), 7.40 (3H, m), 6.40 (1H, s) and 4.75 (2H, s).

EXAMPLE 1B 4-(4-Fluorophenyl)-7-[({5-[(1S)-2,2,2-trifluoro-1-hydroxy-1-methylethyl]-1,3,4-oxadiazol-2-yl}amino)methyl]-2H-chromen-2-one

Step 1: Methyl(2S)-3,3,3-trifluoro-2-hydroxy-2-methylpropanoate

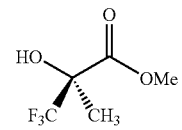

To a solution of (S)-3,3,3-trifluoro-2-hydroxy-2-methyl-propionic acid (3.0 g, 17.4 mmol) in 60 ml of ether was added a solution of diazomethane in ether until a yellow coloration remained. The reaction mixture was then stirred 30 min at room temperature and concentrated to dryness to afford the title compound. $^1$H NMR (400 MHz, acetone-d$_6$): δ 5.67 (s, 1H), 3.85 (s, 3H), 1.57 (s, 3H).

Step 2: (2S)-3,3,3-Trifluoro-2-hydroxy-2-methylpropanohydrazide

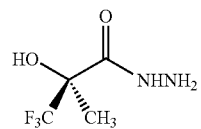

To a solution of methyl(2S)-3,3,3-trifluoro-2-hydroxy-2-methylpropanoate (3.26 g, 19.0 mmol) was added hydrazine monohydrate (2.1 ml). The mixture was heated at 130° C. for 90 min and cooled down to room temperature. After evaporation to dryness, the residue was purified on a small bed of silica gel (100% EtOAc) to afford the title compound.

Step 3: (2S)-2-(5-Amino-1,3,4-oxadiazol-2-yl)-1,1,1-trifluoropropan-2-ol

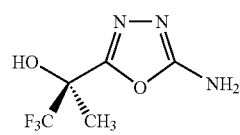

To a solution of (2S)-3,3,3-trifluoro-2-hydroxy-2-methyl-propanohydrazide (3.0 g, 17.5 mmol) in water (17 ml) was added cyanogen bromide (1.87 g, 17.7 mmol) and potassium bicarbonate (1.82 g, 18.1 mmol). The reaction mixture was stirred 30 min at rt until a white precipitate was formed. The precipitate was filtered and washed with water followed by a Step 4: 4-(4-Fluorophenyl)-2-oxo-2H-chromene-7-carbaldehyde

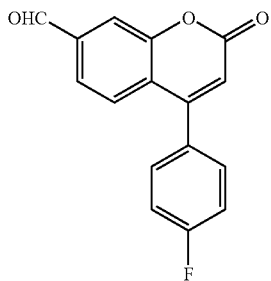

7-(Bromomethyl)-4-(4-fluorophenyl)-2H-chromen-2-one can be prepared as described in Example 1A; its preparation is also described in U.S. Pat. No. 5,552,437. 7-(Bromomethyl)-4-(4-fluorophenyl)-2H-chromen-2-one (11.42 g, 34.3 mmol) and NMO (13.9 g, 102.8 mmol) in 110 mL of dioxane were heated to reflux for 6 h. The solution was cooled to rt and the solvent removed. The crude compound was diluted in EtOAc and washed with $NH_4Cl_{aq}$, water, brine and dried over $MgSO_4$. The solvent was removed to yield the title compound. $^1$H NMR (400 MHz, acetone-$d_6$): δ 10.20 (1H, s), 7.95 (1H, s), 7.85 (1H, m), 7.68 (3H, m), 7.38 (2H, m) and 6.51 (1H, s).

Step 5: 4-(4-Fluorophenyl)-7-[({5-[(1S)-2,2,2-trifluoro-1-hydroxy-1-methylethyl]-1,3,4-oxadiazol-2-yl}amino)methyl]-2H-chromen-2-one

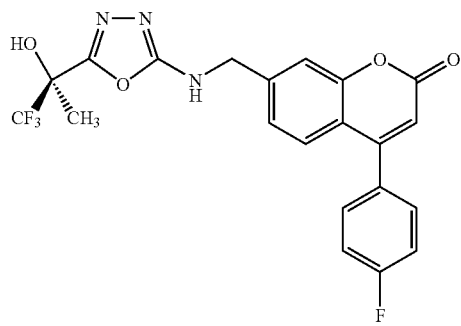

A solution of the previous aldehyde (210 mg, 0.78 mmol), (2S)-2-(5-amino-1,3,4-oxadiazol-2-yl)-1,1,1-trifluoropropan-2-ol (200 mg, 1.02 mmol) and PPTS (20 mg, 0.08 mmol) in 2 ml of toluene was heated under reflux with a Dean-Stark trap for 4 h. The reaction mixture was cooled down and concentrated to dryness. Dry ethanol (2 ml) was then added and the mixture cooled to 0° C. Sodium borohydride (30 mg, 0.78 mmol) was added and the resulting mixture was stirred at 0° C. for 30 min. The reaction mixture was partitioned between aqueous $NH_4Cl$ and EtOAc. The organic phase was washed with brine, dried over anhydrous $MgSO_4$, concentrated and purified on silica gel column (chloroform-ethanol; 95:5) to give the title compound. $^1$H NMR (400 MHz, acetone-$d_6$): δ 7.65 (m, 2H), 7.5 (m, 3H), 7.39 (m, 3H), 6.35 (s, 1H), 6.22 (s, 1H), 4.70 (d, 2H, J=6 Hz), 1.81 (s, 3H).

EXAMPLE 2

4-(4-Fluorophenyl)-7-[({5-[1-hydroxy-1-(trifluoromethyl)propyl]-1,3,4-oxadiazol-2-yl}amino)methyl]-6-methyl-2H-chromen-2-one Step 1: 3-Bromo-4-methylanisole

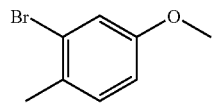

To a suspension of 5-methoxy-2-methylaniline (5.00 g, 36.4 mmol) in water (144 mL) at 10° C., was added conc. $H_2SO_4$ (56 mL), while maintaining internal temperature below 25° C. After 1 h at rt, the mixture was cooled to 3° C. and a solution of sodium nitrite (3.77 g, 54.7 mmol) in water (20 mL) was added dropwise over 30 min, keeping the internal temperature below 5° C. After 1 h at 3° C., the yellow heterogeneous mixture was poured into a 5° C. solution of CuBr (52.0 g, 364 mmol) in 48% aqueous HBr (260 mL). The dark mixture was heated at 60° C. for 2 h, allowed to cool to rt and extracted with $Et_2O$ (3×) (solid $Na_2S_2O_3$ was added in the extraction process for partial decoloration). The combined organics were washed with 1 N NaOH (3×), 10% aq. $Na_2S_2O_3$ and brine, dried ($Na_2SO_4$) and concentrated, affording the title compound as an orange liquid which was used without further purification in the next Step. $^1$H NMR (500 MHz, acetone-$d_6$): δ 7.24 (d, 1H), 7.14 (d, 1H), 6.87 (dd, 1H), 3.80 (s, 3H), 2.31 (s, 3H).

Step 2: (4-Bromo-2-methoxy-5-methylphenyl)(4-fluorophenyl)methanone

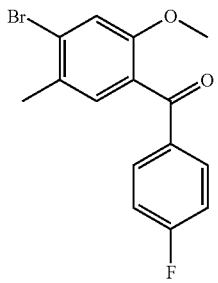

4-Fluorobenzoyl chloride (1.40 mL, 11.9 mmol) was added dropwise to a suspension of $AlCl_3$ (1.73 g, 13.0 mmol) in 1,2-dichloroethane (30 mL) at room temperature. After 15 min a solution of 3-bromo-4-methylanisole (2.17 g, 10.8 mmol) in 1,2-dichloroethane (3 mL) was added dropwise. The resulting mixture was stirred for 2 h, poured into 200 mL of ice-water, stirred for 20 min and extracted with $CHCl_3$ (3×). The combined organics were washed with 5% aq. $NaHCO_3$, brine, dried ($Na_2SO_4$) and concentrated. The residue was subjected to chromatography on silica gel (EtOAc-hexane, 5:95) affording the title compound. $^1$H NMR (500 MHz, acetone-$d_6$): δ 7.86 (m, 2H), 7.38 (s, 1H), 7.31-7.26 (m, 3H), 3.76 (s, 3H), 2.39 (s, 3H).

Step 3: (4-Bromo-2-hydroxy-5-methylphenyl)(4-fluorophenyl)methanone

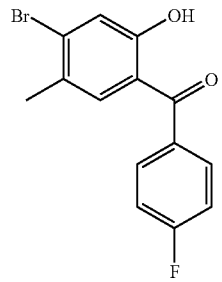

A solution of (4-bromo-2-methoxy-5-methylphenyl)(4-fluorophenyl)methanone (1.80 g, 5.57 mmol) in CH$_2$Cl$_2$ (6 mL) was added over 10 min to a 0° C. solution of BBr$_3$ (1.05 mL, 11.1 mmol) in the same solvent (14 mL) and the resulting mixture was stirred at 0° C. After 1.5 h, the reaction mixture was poured into 200 mL of ice-water, vigorously stirred for 10 min and extracted with CHCl$_3$ (3×). The combined organic extracts were washed with water and brine, dried (Na$_2$SO$_4$) and concentrated, affording the title compound. $^1$H NMR (500 MHz, acetone-d$_6$): δ 11.46 (s, 1H), 7.88 (m, 2H), 7.58 (s, 1H), 7.37 (m, 2H), 7.32 (s, 1H), 2.34 (s, 3H).

Step 4: 7-Bromo-4-(4-fluorophenyl)-6-methyl-2H-chromen-2-one

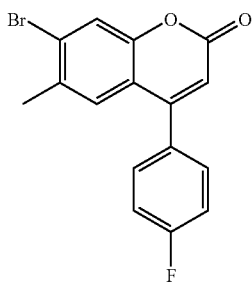

(4-Bromo-2-hydroxy-5-methylphenyl)(4-fluorophenyl)methanone (1.61 g, 5.21 mmol) and methyl(triphenylphosphoranylidene)acetate (2.26 g, 6.77 mmol) were heated in refluxing toluene (15 mL) for 24 h. The reaction mixture was allowed to cool to rt and concentrated. The yellow solid obtained was subjected to column chromatography on silica gel (EtOAc-toluene, 0% to 2%) to afford the title compound. $^1$H NMR (500 MHz, acetone-d$_6$): δ 7.70 (s, 1H), 7.66 (m, 2H), 7.46 (s, 1H), 7.39 (m, 2H), 6.39 (s, 1H), 2.40 (s, 3H).

Step 5: Methyl 4-(4-fluorophenyl)-6-methyl-2-oxo-2H-chromene-7-carboxylate

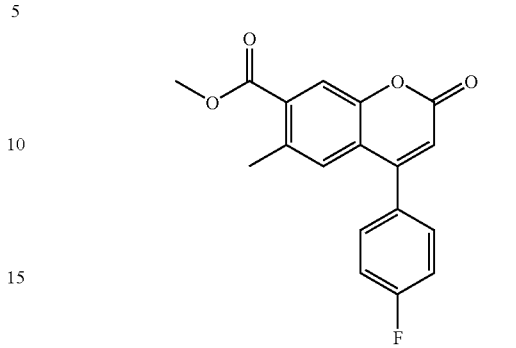

DMSO (17 mL) and Et$_3$N (0.828 mL, 5.94 mmol) were successively added to a suspension of 7-bromo-4-(4-fluorophenyl)-6-methyl-2H-chromen-2-one (0.990 g, 2.97 mmol) and Pd(dppf)Cl$_2$.CH$_2$Cl$_2$ (0.485 g, 0.594 mmol) in MeOH (10 mL). The mixture was heated at 65° C., under an atmosphere of carbon monoxide for 18 h. The reaction mixture was allowed to cool to rt, poured into water (200 mL) and extracted with CHCl$_3$ (3×). The combined organic extracts were washed with water and brine, dried (Na$_2$SO$_4$) and concentrated. The residue was subjected to column chromatography on silica gel (EtOAc-toluene, 3% to 5%) to afford the title compound. $^1$H NMR (500 MHz, acetone-d$_6$): δ 7.85 (s, 1H), 7.69 (m, 2H), 7.44 (s, 1H), 7.40 (m, 2H), 6.47 (s, 1H), 3.94 (s, 3H), 2.54 (s, 3H).

Step 6: 4-(4-Fluorophenyl)-6-methyl-2-oxo-2H-chromene-7-carboxylic acid

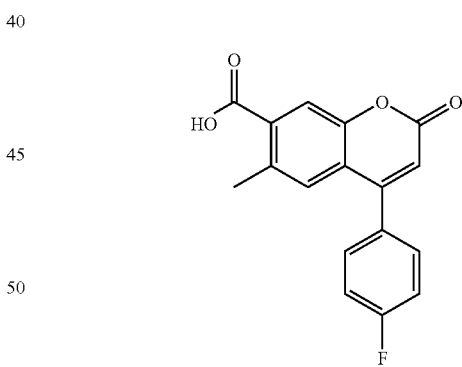

To a solution of methyl 4-(4-fluorophenyl)-6-methyl-2-oxo-2H-chromene-7-carboxylate (0.722 g, 2.31 mmol) in THF (23 mL) was added a 1 N solution of LiOH (11.6 mL, 11.6 mmol), and the mixture was heated at 65° C. for 16 h. At room temperature, the mixture was neutralized with 1 N HCl and concentrated. The residue was stirred with THF (25 mL) and 2 N HCl (50 mL) for 16 h. The precipitate produced was collected by filtration, rinsed with water and dried, affording the title compound that was used without further purification. $^1$H NMR (500 MHz, DMSO-d$_6$): δ 13.40 (br s, 1H), 7.80 (s, 1H), 7.64 (m, 2H), 7.44 (m, 2H), 7.32 (s, 1H), 6.54 (s, 1H), 2.48 (s, 3H).

Step 7: 4-(4-Fluorophenyl)-7-(hydroxymethyl)-6-methyl-2H-chromen-2-one

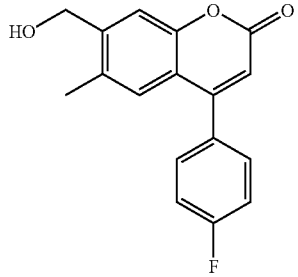

Isobutyl chloroformate (0.775 mL, 5.97 mmol) was added dropwise to 4-(4-fluorophenyl)-6-methyl-2-oxo-2H-chromene-7-carboxylic acid (0.594 g, 1.99 mmol) and Et$_3$N (1.11 mL, 7.96 mmol) in THF (13 mL) at 0° C. After 1 h, a freshly prepared solution of NaBH$_4$ 0.377 g, 9.96 mmol) in water (10 mL) was added rapidly. The reaction mixture was stirred at 0° C. for 1 h, quenched using saturated. NH$_4$Cl and extracted with EtOAc (3×). The combined organic extracts were washed with 1 N HCl, 5% NaHCO$_3$ and brine, dried (Na$_2$SO$_4$) and concentrated. The residue was subjected to column chromatography on silica gel (EtOAc—CHCl$_3$, 30:70, then 35:65, then 40:60) to afford the title compound. $^1$H NMR (400 MHz, acetone-d$_6$): δ 7.65 (m, 2H), 7.53 (s, 1H), 7.38 (m, 2H), 7.26 (s, 1H), 6.30 (s, 1H), 4.76 (d, 2H), 4.55 (t, 1H), 2.26 (s, 3H).

Step 8: 4-(4-Fluorophenyl)-6-methyl-2-oxo-2H-chromene-7-carbaldehyde

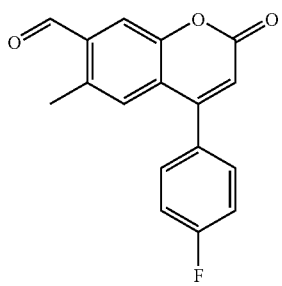

4-(4-Fluorophenyl)-7-(hydroxymethyl)-6-methyl-2H-chromen-2-one (0.487 g, 1.71 mmol) in CH$_2$Cl$_2$ (350 mL) was stirred with activated MnO$_2$ (2.23 g, 25.7 mmol) for 65 h at rt. The reaction mixture was filtered through a pad of celite and the filtrate was concentrated to afford the title compound. $^1$H NMR (500 MHz, acetone-d$_6$): δ 10.40 (s, 1H), 7.86 (s, 1H), 7.70 (m, 2H), 7.46 (s, 1H), 7.42 (m, 2H), 6.53 (s, 1H), 2.66 (s, 3H).

Step 9: 4-(4-Fluorophenyl)-7-[({5-[1-hydroxy-1-(trifluoromethyl)propyl]-3,4-oxadiazol-2-yl}amino)methyl]-6-methyl-2H-chromen-2-one

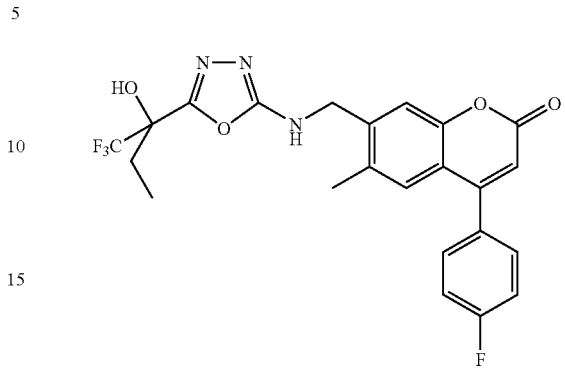

In a round-bottom flask fitted with a condenser and a Dean-Stark trap, 4-(4-fluorophenyl)-6-methyl-2-oxo-2H-chromene-7-carbaldehyde (0.357 g, 1.26 mmol) and 2-(5-amino-1,3,4-oxadiazol-2-yl)-1,1,1-trifluorobutan-2-ol (0.32 g, 1.52 mmol) were heated in refluxing toluene (8 mL) for 2 h in the presence of pyridinium p-toluenesulfonate (32 mg, 0.126 mmol). The mixture was allowed to cool to room temperature and concentrated to dryness. The residue was dissolved in EtOH (6 mL), cooled to 0° C. and NaBH$_4$ (48.0 mg, 1.26 mmol) was added. After 15 min. at 0° C., the reaction was quenched with sat. NH$_4$Cl and extracted with EtOAc (3×). The combined organic extracts were washed with water and brine, dried (Na$_2$SO$_4$) and concentrated. The residue was subjected to column chromatography on silica gel (EtOH—CHCl$_3$, 3% to 4%) to afford the title compound. $^1$H NMR (500 MHz, acetone-d$_6$): δ 7.66 (m, 2H), 7.46 (br s, 2H), 7.39 (m, 2H), 7.33 (s, 1H), 6.32 (s, 1H), 6.09 (br s, 1H), 4.68 (d, 2H), 2.41 (s, 3H), 2.24 (m, 1H), 2.10 (m, 1H), 1.00 (t, 3H).

EXAMPLE 3

7-(2-{[5-(1-Ethyl-1-hydroxypropyl)-1,3,4-thiadiazol-2-yl]amino}ethyl)-4-(4-fluorophenyl)-2H-chromen-2-one

Step 1: 3-(5-Amino-1,3,4-thiadiazol-2-yl)pentan-3-ol

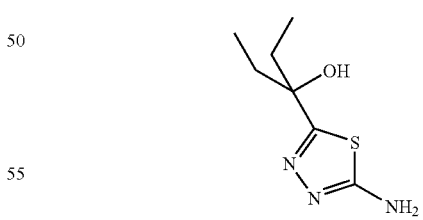

To a −78° C. solution of 2-amino-1,3,4-thiadiazole (commercially available) (2.5 g, 24.72 mmol) in THF (200 mL, 0.1M) was added first n-butyllithium 1.6M hexanes (30.9 mL, 49.4 mmol) followed 15 min later by chlorotrimethylsilane (6.27 mL, 49.4 mmol). The temperature raised to −20° C. for 15 min and cooled back to −78° C. More n-butyllithium 1.6M hexanes (15.45 mL, 24.72 mmol) was added followed 15 min later by 3-pentanone (2.62 mL, 24.72 mmol). The solution was then warmed to rt (overnight). The reaction mixture was quenched with a saturated NH₄Cl solution and THF was removed under vacuum. The aqueous phase was extracted with EtOAc (3×) and the combined organic layers were washed with brine, dried over MgSO₄ and concentrated. The crude residue obtained was purified by column chromatography (100% EtOAc) to yield the title compound. ¹H NMR (400 MHz, acetone-d₆): δ 6.3 (bs, 2H), 4.4 (bs, 1H), 2.0-1.7 (m, 4H), 0.9 (t, 6H).

Step 2: 7-(2-{[5-(1-Ethyl-1-hydroxypropyl)-1,3,4-thiadiazol-2-yl]amino}ethyl)-4-(4-fluorophenyl)-2H-chromen-2-one

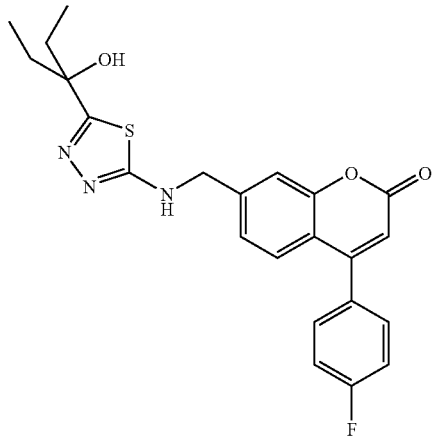

A mixture of 3-(5-amino-1,3,4-thiadiazol-2-yl)pentan-3-ol (0.129 g, 0.689 mmol), 4-(4-fluorophenyl)-2-oxo-2H-chromene-7-carbaldehyde (0.200 g, 0.746 mmol) and acetic acid (7.94 μL, 0.138 mmol) in benzene (2.5 mL) was stirred overnight at reflux with a Dean-Stark trap. After cooling, the mixture was diluted in THF (5 mL) and sodium triacetoxyborohydride (0.731 g, 3.45 mmol) was added. The mixture was then stirred at 45° C. for 3 h. The reaction was quenched with a saturated NaHCO₃ solution and portioned between EtOAc and water. The organic layer was dried over MgSO₄, filtered and concentrated. The crude residue obtained was purified by column chromatography (Hexane-EtOAc-MeOH, 50:50:0 to 0:98:2) to yield the title compound. ¹H NMR (400 MHz, acetone-d₆): δ 8.7 (m, 2H), 7.5 (s, 1H), 7.45 (s, 1H), 7.4 (m, 3H), 6.35 (s, 1H), 4.75 (s, 2H), 4.5 (bs, 1H), 2.0-1.75 (m, 4H), 0.9 (t, 6H).

EXAMPLE 4

7-({[5-(1-Ethyl-1-fluoropropyl)-1,3,4-oxadiazol-2-yl]amino}methyl)-4-(4-fluorophenyl)-2H-chromen-2-one Step 1a:
3-(5-Amino-1,3,4-oxadiazol-2-yl)pentan-3-ol

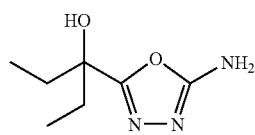

To a solution of ethyl magnesium bromide (200 mmol) in 300 mL of THF at 0° C. was added a suspension of ethyl 5-amino-1,3,4-oxadiazole-2-carboxylate (8.00 g, 50.9 mmol; *Chemical Abstract*, 1966, 64, 3558a) in THF. The reaction mixture was brought to rt and 30 min later quenched with NH₄Cl. After extraction with EtOAc and drying over MgSO₄, the solvent was removed. The crude product thus obtained was triturated, filtered and dried to yield the title compound.

Step 1b:
3-(5-Amino-1,3,4-oxadiazol-2-yl)pentan-3-ol

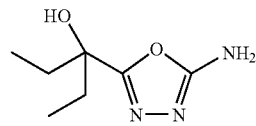

A mixture of methyl 2-ethyl-2-hydroxybutanoate (19.7 g, 134.7 mol) and hydrazine hydrate (14 mL) was heated to 130° C. for 4 h. The mixture was cooled to rt and excess reagent removed under vacuum to yield of the hydrazide. To this hydrazide and KHCO₃ (13.8 g, 138 mmol) in 150 mL of water was added portionwise BrCN (13.8 g, 131 mmol). After 90 min of stirring, the white solid was filtered, washed with ether and dried to yield the title compound. ¹H NMR (400 MHz, acetone-d₆): δ 6.20 (bs, 2H), 4.25 (s, 1H), 1.85 (m, 4H), 0.88 (t, 6H).

Step 2: 7-({[5-(1-Ethyl-1-hydroxypropyl)-1,3,4-oxadiazol-2-yl]amino}methyl)-4-(4-fluorophenyl)-2H-chromen-2-one

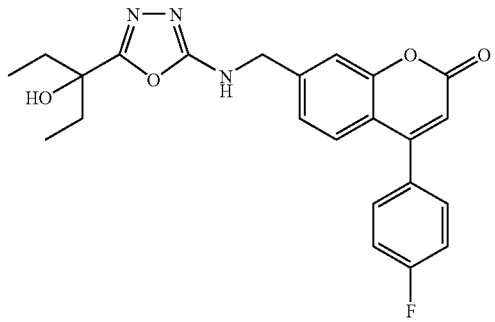

A mixture of 3-(5-amino-1,3,4-oxadiazol-2-yl)pentan-3-ol (0.446 g, 2.6 mmol) and 4-(4-fluorophenyl)-2-oxo-2H-chromene-7-carbaldehyde (0.350 g, 1.3 mmol) in 5 mL of toluene was refluxed with a Dean-Stark trap overnight. After cooling to rt the solvent was removed and the crude imine diluted in ethanol (8 ml) at 0° C. Solid NaBH₄ (49 mg) was added to the solution and after 30 min of stirring aqueous NH₄Cl was added to destroy the excess hydride. After dilution with EtOAc-brine, the organic phase was dried with MgSO₄. Purification on silica gel with toluene-EtOAc (2:8) gave the title compound. ¹H NMR (400 MHz, acetone-d₆): δ 7.67 (m, 2H), 7.48 (m, 2H), 7.37 (m, 3H), 7.19 (bt, 1H), 6.33 (s, 1H), 4.66 (m, 2H), 4.31 (s, 1H), 1.85 (m, 4H), 0.85 (t, 6H).

Step 3: 7-({[5-(1-Ethyl-1-fluoropropyl)-1,3,4-oxa-diazol-2-yl]amino}methyl)-4-(4-fluorophenyl)-2H-chromen-2-one

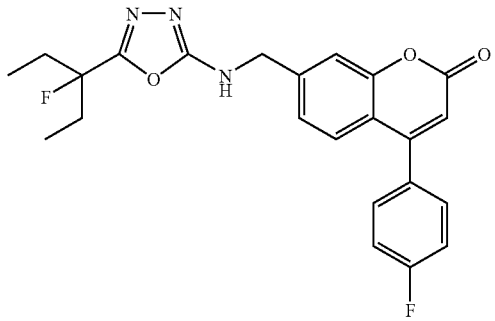

A solution of imine obtained in the previous step (270 mg, 0.641 mmol) in CH$_2$Cl$_2$ was added dropwise to a solution of (diethylamino)sulphur trifluoride (100 µL, 0.77 mmol) in CH$_2$Cl$_2$ precooled to −78° C. The solution was stirred at −78° C. 5 min, and warmed to room temperature. After 40 min at room temperature, the reaction mixture was decanted rapidly to a solution of NaBH$_4$ (0.20 g, 5.3 mmol) in EtOH (10 mL), and stirred vigorously at room temperature for 5 min. The reaction mixture was partitioned between EtOAc and a saturated aq. solution of NH$_4$OAc/NaCl. The phases were separated and the aqueous phase extracted with EtOAc. The combined organic phases were dried over anhydrous MgSO$_4$, filtered and concentrated in vacuo. The residue was chromatographed on silica gel (20-60% EtOAc/hexanes) to afford the title compound. $^1$H NMR (400 MHz, CDCl$_3$): δ 7.60-7.67 (m, 2H), 7.43-7.52 (m, 3H), 7.34-7.40 (m, 3H), 6.32 (s, 1H), 4.68 (d, 2H), 1.95-2.17 (m, 4H), 0.91 (t, 6H).

EXAMPLE 5

7-(1-{[5-(1-Ethyl-1-hydroxypropyl)-1,3,4-oxadiazol-2-yl]amino}ethyl)-4-(4-fluorophenyl)-2H-chromen-2-one

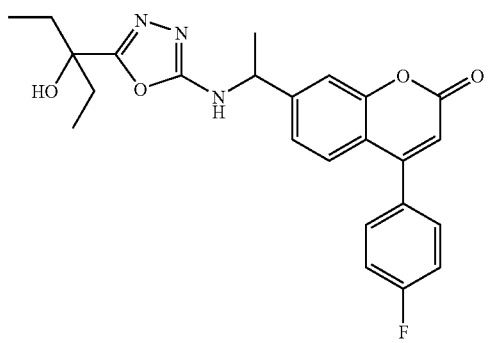

To a solution of the imine, prepared as described in Example 4, step 2, (0.159 g, 0.37 mmol) in 5 mL of THF at −90° C. was added methylmagnesium bromide (0.79 mmol). The reaction mixture was brought to 0° C. and quenched with NH$_4$Cl. After extraction with EtOAc, drying with MgSO$_4$, and evaporation, the crude material was purified on silica gel with toluene-EtOAc (2:8) to yield the title compound. $^1$H NMR (400 MHz, acetone-d$_6$) δ: 7.66 (m, 2H), 7.35-7.52 (m, 5H), 7.19 (d, 1H), 6.33 (s, 1H), 4.95 (m, 1H), 4.23 (s, 1H), 1.72 (m 4H), 1.63 (d, 3H), 0.80 (m, 6H).

EXAMPLE 6A 7-bromo-4-pyridin-3-yl-2H-chromen-2-one can be prepared as follows

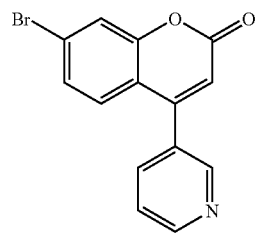

Commercially available 7-hydroxy-4-(3-pyridyl)coumarin (1.48 g, 6.19 mmol) and triphenylphosphine dibromide (5.22 g, 12.4 mmol) are heated in a sand bath at 320-350° C. for 1.5 h. The cooled solid is taken up with ethanol (200 ml) and silica gel (100 g) and evaporated to dryness. Column chromatography (toluene/acetone; 80:20) affords 7-bromo-4-pyridin-3-yl-2H-chromen-2-one.

EXAMPLE 6B 7-({5-[Dicyclopropyl(hydroxyl)methyl]-1,3,4-thia-diazol-2-yl}thio)-4-pyridine-3-yl-2H-chromen-2-one

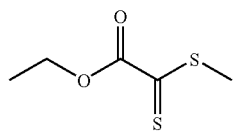

Step 1: Ethyl(methylthio)(thioxo)acetate

To a mixture of sulfur (5.23 g, 163 mmol) in DMF (100 ml) was added triethylamine (34.1 ml, 245 mmol) and ethyl chloroacetate (10 g, 81.6 mmol). After 3.5 h iodomethane (5.59 ml, 89.8 mmol) was added and the mixture was stirred 1 h at rt. Et$_2$O-water was added and the organic layer was separated. The organic phase was wash with water (3×), brine, dried over anhydrous Na$_2$SO$_4$ and the solvent removed to give the title compound which was used without further purification for the next step. $^1$H NMR (400 MHz, acetone-d$_6$): 4.38 (q, 2H), 2.72 (s, 3H), 1.34 (t, 3H).

Step 2: Ethyl 5-mercapto-1,3,4-thiadiazole-2-carboxylate

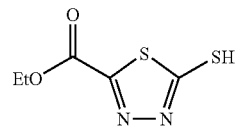

Ethyl(methylthio)(thioxo)acetate (20.0 g, 122 mmol) and potassium hydrazinecarbodithioate (R. S. Drago et al., *JACS* (1983) 105, 2287) (17.8 g, 122 mmol) were reflux overnight in ethanol (500 ml). The solution was concentrated and EtOAc was added. The organic phase was washed with 1M HCl, brine and dried over anhydrous $Na_2SO_4$. The solvent was evaporated and the residue purified on silica gel (hexanes-acetone, 80:20) to give the title compound. $^1$H NMR (400 MHz, acetone-$d_6$): 4.43 (q, 2H), 1.38 (t, 3H).

Step 3: Dicyclopropyl(5-mercapto-1,3,4-thiadiazol-2-yl)methanol

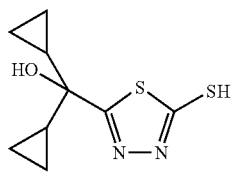

To a solution of cyclopropylmagnesiumbromide (37 ml, 0.5 M/THF, 18.4 mmol at 0° C. was slowly added a THF solution of ethyl 5-mercapto-1,3,4-thiadiazole-2-carboxylate (1 g, 5.3 mmol). When half the solution was added, the cooling bath was removed and the rest of the solution was added. The mixture was stirred at room temperature for 4 hours then partitioned between aqueous $NH_4Cl$ and $Et_2O$. The layers were separated and the aqueous phase was extracted with $Et_2O$. The combined organic layers were washed with brine and dried over anhydrous $Na_2SO_4$. The solvent was evaporated and the residue chromatographed on silica gel (hexanes:acetone, 95:5) to give the title compound. $^1$H NMR (400 MHz, acetone-$d_6$): 4.75 (s, 1H), 1.39-1.26 (m, 2H), 0.67-0.38 (m, 8H).

Step 4: 7-({5-[Dicyclopropyl(hydroxyl)methyl]-1,3,4-thiadiazol-2-yl}thio)-4-pyridine-3-yl-2H-chromen-2-one

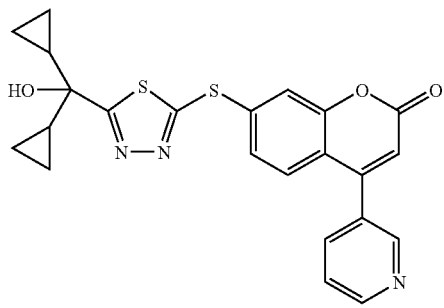

KOH (0.089 g, 1.59 mmol) was added to a solution of dicyclopropyl(5-mercapto-1,3,4-thiadiazol-2-yl)methanol (0.363 g, 1.60 mmol) in dry MeOH. When a solution was obtained, the reaction mixture was concentrated to dryness. Dry toluene was then added and the mixture was concentrated to dryness again. The residue was dissolved in NMP, 7-bromo-4-pyridin-3-yl-2H-chromen-2-one (400 mg, 1.32 mmol) was added and the resulting mixture was stirred at 120° C. for 16 h. The reaction mixture was cooled and partitioned between aqueous $NH_4OAc$ and EtOAc. The organic phase was washed with brine, dried over anhydrous $Na_2SO_4$, concentrated and purified on silica gel column (toluene-acetone, 90:10 to 70:30) to give the title compound. $^1$H NMR (400 MHz, $CDCl_3$): δ 8.82 (d, 1H), 8.72 (s,1H), 7.81 (dt, 1H), 7.64 (s, 1H), 7.58-7.50 (m, 1H), 7.48-7.41 (m, 2H), 6.46 (s, 1H), 2.57 (s, 1H), 1.40-1.31 (m, 2H), 0.69-0.57 (m, 6H), 0.50-0.44 (m, 1H).

EXAMPLE 7

(+) and (−)-4-(4-Fluorophenyl)-7-[({5-[1-hydroxy-1-(trifluoromethyl)propyl]-1,3,4-oxadiazol-2-yl}amino)methyl]-2H-chromen-2-one Step 1: Ethyl 2-hydroxy-2-(trifluoromethyl)butanoate

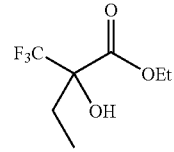

To a −78° C. solution of ethyl trifluoropyruvate (129.0 g 758 mmol) in ether was added dropwise within 90 min a solution of EtMgBr 3.0 M in ether (252 mL). The solution was brought over one 1 h to ca. −10° C. and poured over 2 L of saturated $NH_4Cl$. The layers were separated and the aqueous phase extracted with ether (3×500 mL). The organic phases were combined, dried over MgSO4 and the solvent removed. Distillation at 50-65° C. (30 mm Hg) gave the title compound. $^1$H NMR (400 MHz, acetone-$d_6$): δ 5.4 (s, 1H), 4.35 (q, 2H), 2.07 (m, 1H), 1.83 (m, 1H), 1.3 (t, 3H) and 0.93 (t, 3H).

Step 2: 2-Hydroxy-2-(trifluoromethyl)butanohydrazide

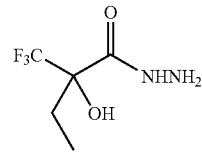

The ethyl ester of step 1 (50.04 g, 250 mmol) and hydrazine hydrate (25.03 g, 50 mmol) were heated at 80° C. for 18 h. The excess hydrazine was removed under vacuum and the crude product was filtered through a pad of silica gel with EtOAc-Hexane (ca. 3 L) to furnish the title compound. $^1$H NMR (400 MHz, acetone-$d_6$): δ 9.7 (s, 1H), 6.10 (s, 1H), 2.25 (m, 1H), 1.85 (m, 1H) and 0.95 t, (3H).

Step 3: 2-(5-Amino-1,3,4-oxadiazol-2-yl)-1,1,1-trifluorobutan-2-ol

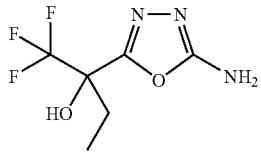

To hydrazide (34.07 g, 183 mmol) of step 2 in 275 mL of water was added KHCO₃ (18.33 g, 183 mmol) followed by BrCN (19.39 g, 183 mmol) portionwise. After 3 h, the solid was filtered, washed with cold water and dried to afford the title compound. Additional compound could be recovered from the aqueous phase by extraction (ether-hexane, 1:1). $^1$H NMR (400 MHz, acetone-$d_6$): δ 6.54 (s, 2H), 6.01 (s, 1H), 2.22 (m, 1H), 2.08 (m, 1H) and 0.99 (m, 3H).

Step 4: 4-(4-Fluorophenyl)-7-[({5-[1-hydroxy-1-(trifluoromethyl)propyl]-1,3,4-oxadiazol-2-yl}amino)methyl]-2H-chromen-2-one

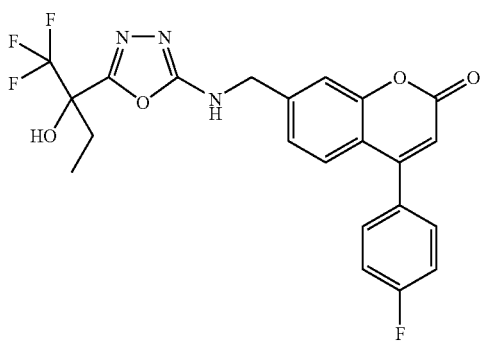

A mixture of oxadiazole (14.41 g, 68.2 mmol) of step 3 and 4-(4-fluorophenyl)-2-oxo-2H-chromene-7-carbaldehyde (14.1 g, 52.5 mmol) in toluene (160 mL) with 10% of PPTS was brought to reflux and let go overnight. The system was equipped with a Dean-Stark trap to collect water. The solvent was removed and the crude oil ($^1$H NMR (400 MHz, acetone-$d_6$): δ 9.33 (1H, s, imine)) obtained was diluted in EtOH (ca. 75 mL) at 0° C. To this solution was added NaBH₄ (1.9 g) portionwise and the reaction was quenched with a solution of NH₄Cl after 45 min. The mixture was saturated with NaCl and extracted with EtOAc (3×200 mL). The organic phases were combined and dried over MgSO₄. Purification over silica gel chromatography using toluene-EtOAc (55:45) gave the title compound. $^1$H NMR (400 MHz, acetone-$d_6$): δ 7.65 (m, 2H), 7.50 (m, 3H), 7.38 (m, 3H), 6.35 (s, 1H), 6.06 (s, 1H), 4.70 (m, 2H), 2.21 (m, 1H), 2.11 (m, 1H) and 0.98 (t, 3H).

Step 5: Separation on chiral HPLC column of (+) and (−) enantiomers of 4-(4-fluorophenyl)-7-[({5-[1-hydroxy-1-(trifluoromethyl)propyl]-1,3,4-oxadiazol-2-yl}amino)methyl]-2H-chromen-2-one

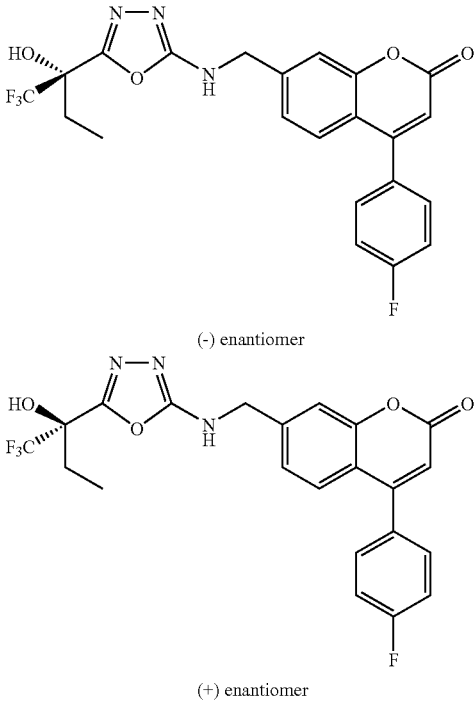

(−) enantiomer (+) enantiomer

A solution of (±)-4-(4-fluorophenyl)-7-[({5-[1-hydroxy-1-(trifluoromethyl)propyl]-1,3,4-oxadiazol-2-yl}amino)methyl]-2H-chromen-2-one (0.5-0.6 g) in EtOH-Hexane (30:70, ca. 40 mL) was injected onto a CHIRALPAK AD® preparative (5 cm×50 cm) HPLC column (eluting with EtOH/Hexane, 30/70 with UV detection at 280 nm). The enantiomers were separated with the faster eluting enantiomer having a retention time of ~34 min for the (−)-enantiomer and the slower eluting enantiomer having a retention time of ~49 min for the (+)-enantiomer.

EXAMPLE 8

4-(4-Fluorophenyl)-7-{[{5-[1-hydroxy-1-(trifluoromethyl)propyl]-1,3,4-oxadiazol-2-yl}(methyl)amino]methyl}-2H-chromen-2-one Step 1: 4-(4-Fluorophenyl)-7-{[{5-[1-hydroxy-1-(trifluoromethyl)propyl]-1,3,4-oxadiazol-2-yl}(methyl)amino]methyl}-2H-chromen-2-one

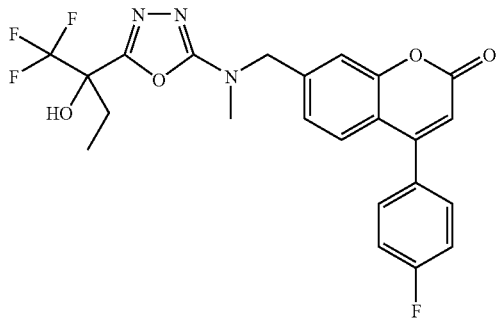

The (−) isomer of 4-(4-fluorophenyl)-7-[({5-[1-hydroxy-1-(trifluoromethyl)propyl]-1,3,4-oxadiazol-2-yl}amino)methyl]-2H-chromen-2-one (0.100 g, 0.22 mmol), methyl iodide (2 mL) and K₂CO₃ (0.061 g 0.44 mmol) were heated at 50° C. until the disappearance of starting material. The mixture was cooled to rt and diluted with EtOAc-water. The organic layer was separated, dried and the solvent removed. Purification on silica gel (toluene-acetone, 8:2) gave the title compound. ¹H NMR (400 MHz, acetone-d₆): δ 7.68 (m, 2H), 7.51 (d, 1H), 7.48 (s, 1H), 7.39 (m, 3H), 6.49 (s, 1H), 6.12 (s, 1H), 4.8 (q, 2H), 3.17 (s, 3H), 2.26 (m, 1H), 2.09 (m, 1H), 1.02 (t, 3H).

EXAMPLE 9A 7-bromo-4-(2-methyl-1,3-thiazol-4-yl)-2H-chromen-2-one can be prepared as follows

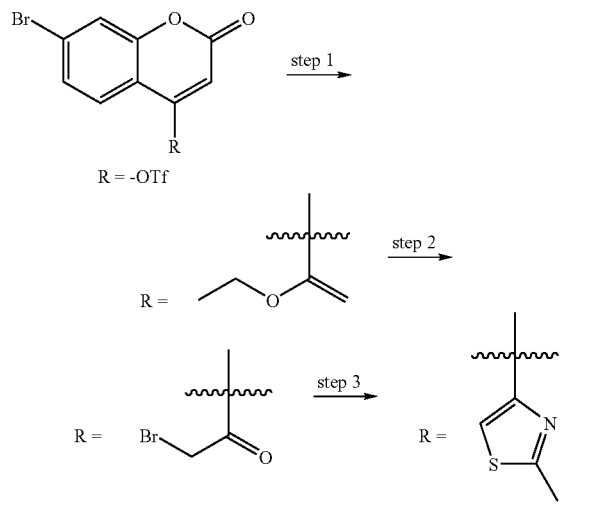

Step 1:
7-bromo-4-(1-ethoxyvinyl)-2H-chromen-2-one

To a solution of 7-bromo-4-trifluoromethanesulfonyloxycoumarin (5.1 g, 13.7 mmol) in dioxane is added tributyl(1-ethoxyvinyl)tin (4.8 mL, 14.2 mmol), (Ph₃P)₄Pd (0.790 g, 0.7 mmol) and LiCl (1.74 g, 41 mmol). The mixture is refluxed for 4 h, cooled and partitioned between aqueous NH₄Cl and EtOAc. The layers are separated and the aqueous phase is extracted with EtOAc. The combined organic layers are washed with brine and dried over anhydrous Na₂SO₄. The solvent is evaporated and the residue is chromatographed on silica gel (CH₂Cl₂/EtOAc; 95:5) and triturated in hexane/Et₂O to give the title compound.

Step 2: 7-bromo-4-(bromoacetyl)-2H-chromen-2-one

To a solution of 7-bromo-4-(1-ethoxyvinyl)-2H-chromen-2-one (2.0 g, 6.8 mmol) in THF and H₂O is added N-bromosuccinimide (1.3 g, 14.2 mmol) with stirring for 30 min. Toluene is added and the solvent is evaporated. The residue is chromatographed on silica gel (hexane/EtOAc; 80:20) to give the title compound.

Step 3: 7-bromo-4-(2-methyl-1,3-thiazol-4-yl)-2H-chromen-2-one

To a solution of 7-bromo-4-(bromoacetyl)-2H-chromen-2-one (0.605 g, 1.7 mmol) in DMF is added thioacetamide (0.138 g, 1.8 mmol). The mixture is stirred 24 h at rt and at 100° C. overnight. Once cool to rt, it is partitioned between aqueous NH₄Cl and EtOAc. The layers are separated and the aqueous phase is extracted with EtOAc. The combined organic layers are washed with brine and dried over anhydrous Na₂SO₄. The solvent is evaporated and the residue swished in hexanes/Et₂O to give the title compound.

EXAMPLE 9B

7-[({5-[1-Hydroxy-1-(trifluoromethyl)propyl]-1,3,4-oxadiazol-2-yl}amino)methyl]-4-(2-methyl-1,3-thiazol-4-yl)-2H-chromen-2-one Step 1: Methyl 4-(2-methyl-1,3-thiazol-4-yl)-2-oxo-2H-chromene-7-carboxylate

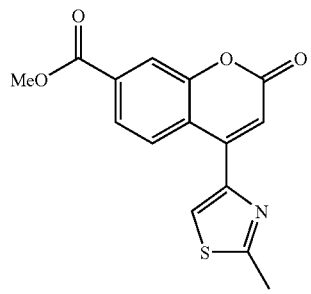

To a solution of 7-bromo-4-(2-methyl-1,3-thiazol-4-yl)-2H-chromen-2-one (1.17 g, 3.63 mmol) in DMSO (21 ml) and methanol (12 ml) was added triethylamine (1.0 mL, 7.26 mmol) and [Pd(dppf)Cl₂]₂—CH₂Cl₂ (0.593 g, 0.73 mmol). The reaction mixture was stirred overnight at 65° C. with a balloon of carbon monoxide. After cooling to rt, the reaction mixture was diluted with EtOAc—CH₂Cl₂ (9:1) washed with water (3x) and brine. The organic phase was dried over MgSO₄ and evaporated to dryness. The residue was purified on silica gel (hexanes-EtOAc, 8:2) to afford the title compound. ¹H NMR (400 MHz, acetone-d₆): δ 8.45 (m, 1H), 8.12 (s, 1H), 7.92 (m, 2H), 6.80 (s, 1H), 3.97 (s, 3H), 2.85 (s, 3H).

Step 2: 4-(2-Methyl-1,3-thiazol-4-yl)-2-oxo-2H-chromene-7-carboxylic acid

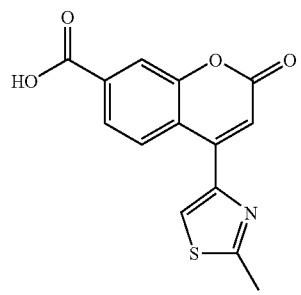

To a solution of methyl 4-(2-methyl-1,3-thiazol-4-yl)-2-oxo-2H-chromene-7-carboxylate (1.0 g, 3.32 mmol) in THF (33 ml) was added lithium hydroxide 1 M (16.6 ml, 16.6 mmol). The reaction was heated at 65° C. for 90 min, cooled to rt and evaporated. A solution of HCl 2N was then added to the residue and the mixture stirred for 1 h. The powder was filtered to give the title compound. ¹H NMR (400 MHz, DMSO-d₆): δ 8.37 (m, 1H), 8.28 (s, 1H), 7.87 (m, 2H), 6.85 (s, 1H), 2.80 (s, 3H).

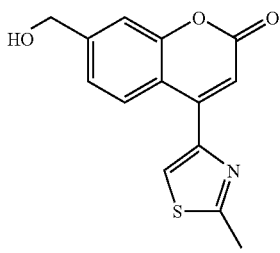

Step 3: 7-(Hydroxymethyl)-4-(2-methyl-1,3-thiazol-4-yl)-2H-chromen-2-one

To a solution of 4-(2-methyl-1,3-thiazol-4-yl)-2-oxo-2H-chromene-7-carboxylic acid (0.692 g, 2.41 mmol) in THF (16 ml) at 0° C. was added triethylamine (1.3 ml, 9.63 mmol) followed by isobutyl chloroformate (0.94 ml, 7.23 mmol) over 15 min. The reaction mixture was stirred at 0° C. for 1 h and sodium borohydride (0.456 g, 12.0 mmol) in water (12 ml) was added. The reaction mixture was stirred 1 h at 0° C., quenched with a solution of NH₄Cl and extracted with EtOAc. The organic phase was washed with brine, dried over MgSO₄ and evaporated to dryness. The residue was purified by chromatography on silica gel (hexanes-EtOAc, 4:6 to 2:8) to give the title compound. ¹H NMR (400 MHz, acetone-d₆): δ 8.22 (m, 1H), 8.05 (s, 1H), 7.40 (s, 1H), 7.35 (m, 1H), 6.62 (s, 1H), 4.80 (m, 2H), 4.55 (m, 1H), 2.82 (s, 3H).

Step 4: 4-(2-Methyl-1,3-thiazol-4-yl)-2-oxo-2H-chromene-7-carbaldehyde

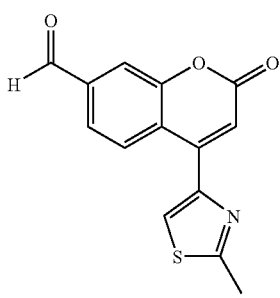

To a solution of 7-(hydroxymethyl)-4-(2-methyl-1,3-thiazol-4-yl)-2H-chromen-2-one (0.387 g, 1.42 mmol) in CH₂Cl₂ (7 ml) was added MnO₂ (1.85 g, 21.2 mmol) and stirred at rt for 4 h. A second portion of MnO₂ (1.85 g, 21.2 mmol) was added and 3 h later the reaction mixture was filtered on celite, evaporated to dryness and purified by trituration in CH₂Cl₂-MeOH (9:1) to give the title compound. ¹H NMR (400 MHz, acetone-d₆): δ 10.12 (s, 1H), 8.45 (m, 1H), 8.31 (s, 1H), 7.95 (s, 1H), 7.85 (m, 1H), 6.9 (s, 1H), 2.80 (s, 3H).

Step 5: 7-[({5-[1-Hydroxy-1-(trifluoromethyl)propyl]-1,3,4-oxadiazol-2-yl}amino)methyl]-4-(2-methyl-1,3-thiazol-4-yl)-2H-chromen-2-one

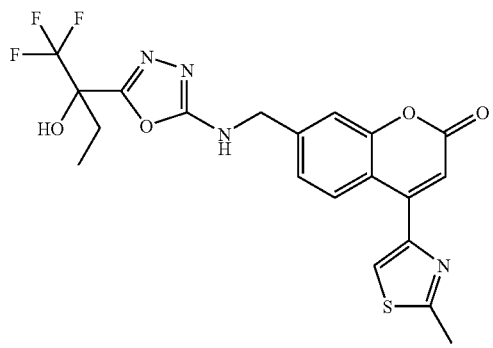

To a solution of 4-(2-methyl-1,3-thiazol-4-yl)-2-oxo-2H-chromene-7-carbaldehyde (0.200 g, 0.74 mmol) and 2-(5-amino-1,3,4-oxadiazol-2-yl)-1,1,1-trifluorobutan-2-ol (0.202 g, 0.96 mmol) in toluene (2 ml) was added PPTS (0.019 g, 0.07 mmol). The reaction mixture was heated under reflux with a Dean-Stark trap for 6 h. After evaporation, the residue was diluted in EtOH (2 ml), cooled to 0° C. and sodium borohydride (28 mg, 0.74 mmol) was added. After 15 min, the reaction was quenched with a saturated solution of NH₄Cl, extract with EtOAc then washed with water and brine. The solvent was evaporated and the residue chromatographed on silica gel (chloroform-ethanol, 95:5) to give the title compound. ¹H NMR (400 MHz, acetone-d₆): δ 8.27 (d, 1H), 8.09 (s, 1H), 7.45 (m, 3H), 6.66 (s, 1H), 6.08 (s, 1H), 4.7 (d, 2H), 2.83 (s, 3H), 2.22 (m, 1H), 2.10 (m, 1H), 0.98 (m, 3H).

What is claimed is:
1. A compound of structural Formula Ia

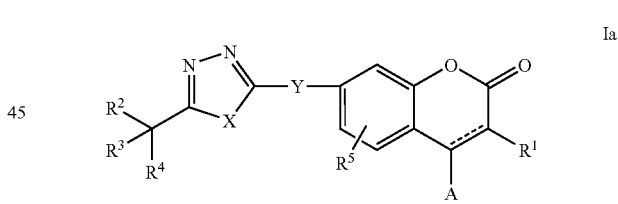

or a pharmaceutically acceptable salt or ester thereof wherein:

- - - - is selected from a single and a double bond;

"A" is selected from the group consisting of (a) phenyl, (b) —CH₂— phenyl, and (c) naphthalenyl;

and wherein A is optionally mono- or di-substituted with a substituent independently selected at each occurrence from the group consisting of (i) —F (ii) —Cl, (iii) —C₁₋₃alkyl optionally substituted with one or more of halo, (iv) —OC₁₋₃alkyl optionally substituted with one or more of halo, (v) —OC₃₋₆cycloalkyl, (vi) —CH₂OH, (vii) —COOR¹, (viii) —CN and (ix) —NR¹⁰R¹¹;

X is selected from —O— and —S—;

Y is selected from —NR⁶—CHR⁷ and —NR⁸—C(O)— wherein the nitrogen in Y is linked to the 5-membered heterocyclic moiety of Formula Ia and the carbon in Y is linked to the bicyclic heterocyclic moiety of Formula Ia;

R¹ is selected from the group consisting of —H, —C$_{1-6}$ alkyl and —C$_{3-6}$ cycloalkyl;

R² is selected from the group consisting of —H, —OH, —F, —C$_{1-3}$alkyl, —OC$_{1-3}$alkyl and —OC(O)—C$_{1-3}$ alkyl;

R³ is selected from the group consisting of —H, —C$_{1-6}$ alkyl, —C$_{1-6}$alkyl substituted with one or more of fluoro, —C$_{1-6}$alkyl substituted with R⁹, —C$_{2-6}$alkenyl, —C$_{3-6}$cycloalkyl, —C$_{5-7}$cycloalkenyl and -Z;

R⁴ is selected from the group consisting of —H, —C$_{1-6}$ alkyl, —C$_{1-6}$alkyl substituted with one or more of fluoro, —C$_{1-6}$alkyl substituted with R⁹, —C$_{2-6}$alkenyl, —C$_{3-6}$cycloalkyl, —C$_{5-7}$cycloalkenyl and -Z;

or R³ and R⁴ together represent oxo;

or R³ and R⁴ are joined together with the carbon to which they are attached to form a ring selected from the group consisting of a —C$_{3-6}$cycloalkyl ring and a —C$_{5-7}$cycloalkenyl ring, provided that when R³ and R⁴ are joined together with the carbon to which they are attached to form a —C$_{5-7}$cycloalkenyl ring, there is no double bond at the C-1 position in the ring;

or R², R³ and R⁴ are joined together with the carbon to which they are attached to form a cycloalkenyl ring selected from:

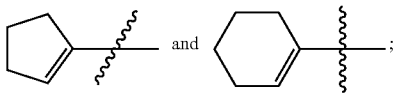

R⁵ is absent or is a substituent selected from the group consisting of —C$_{1-6}$ alkyl, —C$_{3-6}$ cycloalkyl and halo;

R⁶ is selected from the group consisting of (a) —H, (b) —C$_{1-4}$ alkyl, (c) —C(O)C$_{1-4}$ alkyl, and (d) —C(O)phenyl optionally substituted with —C$_{1-4}$ alkyl;

R⁷ is selected from the group consisting of (a) —H, (b) —C$_{1-4}$ alkyl, (c) —C$_{3-6}$cycloalkyl, and (d) phenyl optionally mono- or di-substituted with a substituent independently selected at each occurrence from the group consisting of —C$_{1-4}$ alkyl, —F and —Cl;

R⁸ is selected from the group consisting of —H and —C$_{1-4}$ alkyl;

R⁹ is selected from the group consisting of —COOR¹, —C(O)H, —CN, CR¹R¹OH, —OR¹, —S—C$_{1-6}$alkyl and —S—C$_{3-6}$ cycloalkyl;

R¹⁰ is selected from the group consisting of —H, —C$_{1-6}$ alkyl, —C$_{3-6}$ cycloalkyl and —COOR¹;

R¹¹ is selected from the group consisting of —H, —C$_{1-6}$ alkyl and —C$_{3-6}$ cycloalkyl; and Z is selected from the group consisting of phenyl, —CH$_2$—phenyl and —CH$_2$-dioxolanyl, and wherein Z is optionally mono- or di-subsituted with a substituent independently selected at each occurrence from the group consisting of (i) —F, (ii) —Cl, (iii) —C$_{1-3}$alkyl optionally substituted with one or more of halo, (iv) —OC$_{1-3}$ alkyl optionally substituted with one or more of halo, (v) —OC$_{3-6}$cycloalkyl, (vi) —CH$_2$OH, (vii) —COOR¹, (viii) —CN and (ix) —NR¹⁰R¹¹.

2. The compound of claim 1 having structural Formula Ib

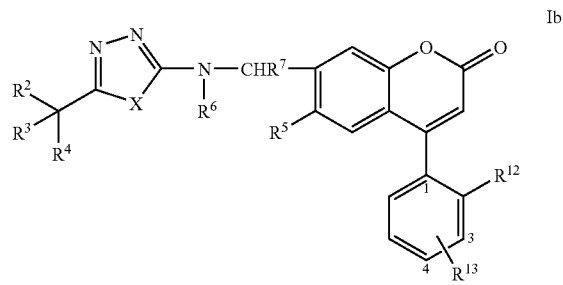

or a pharmaceutically acceptable salt or ester thereof wherein R¹² is selected from the group consisting of —H and —F; and R¹³ is absent or is a substituent at the 3- or 4-position and is selected from the group consisting of (i) —F, (ii) —Cl, (iii) —C$_{1-3}$alkyl optionally substituted with one or more of halo, (iv) —OC$_{1-3}$alkyl optionally substituted with one or more of halo, (v) —OC$_{3-6}$cycloalkyl, (vi) —CH$_2$OH, (vii) —COOR¹, (viii) —CN and (ix) —NR¹⁰R¹¹.

3. The compound of claim 2 having structural Formula I

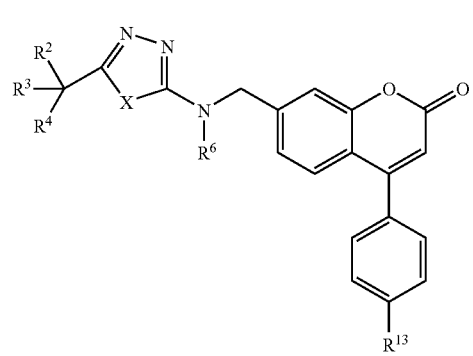

or a pharmaceutically acceptable salt or ester thereof.

4. The compound of claim 1 selected from the group consisting of:

4-(4-fluorophenyl)-7-{[{5-[1-hydroxy-1-(trifluoromethyl)propyl]-1,3,4-oxadiazol-2-yl}(isopropyl) amino] methyl}-2H-chromen-2-one;

4-(4-fluorophenyl)-7-{[{5-[1-hydroxy-1-(trifluoromethyl)propyl]-1,3,4-oxadiazol-2-yl}amino]methyl}-6-methyl-2H-chromen-2-one;

N-{[4-(4-fluorophenyl)-2-oxo-2H-chromen-7-yl]methyl}-N-{5-[1-hydroxy-1-(trifluoromethyl)propyl]-1,3,4-oxadiazol-2-yl}acetamide;

4-(4-fluorophenyl)-7-[({5-[1-hydroxy-1-(trifluoromethyl)propyl]-1,3,4-oxadiazol-2-yl}amino)methyl]-6-methyl-2H-chromen-2-one;

4-(4-fluorophenyl)-7-({[5-(1-hydroxy-1-phenylethyl)-1, 3,4-oxadiazol-2-yl]amino}methyl)-2H-chromen-2-one;

4-(4-fluorophenyl)-7-[({5-[2,2,2-trifluoro-1-hydroxy-1-(trifluoromethyl)ethyl]-1,3,4-oxadiazol-2-yl}amino) methyl]-2H-chromen-2-one;

4-(4-fluorophenyl)-7-[({5-[(1S)-2,2,2-trifluoro-1-hydroxy-1-methylethyl]-1,3,4-oxadiazol-2-yl}amino)methyl]-2H-chromen-2-one;

4-(4-fluorophenyl)-7-{[{5-[1-hydroxy-1-(trifluoromethyl)propyl]-1,3,4-oxadiazol-2-yl}(methyl)amino]methyl}-2H-chromen-2-one;

4-(4-fluorophenyl)-7-[({5-[(1R)-2,2,2-trifluoro-1-hydroxy-1-methylethyl]-1,3,4-oxadiazol-2-yl}amino)methyl]-2H-chromen-2-one;

3-{7-[({5-[1-hydroxy-1-(trifluoromethyl)propyl]-1,3,4-oxadiazol-2-yl}amino)methyl]-2-oxo-2H-chromen-4-yl}benzonitrile;

4-(4-fluorophenyl)-7-({[5-(2,2,3,3,3-pentafluoro-1-hydroxy-1-methylpropyl)-1,3,4-oxadiazol-2-yl]amino}methyl)-2H-chromen-2-one;

4-(4-fluorophenyl)-7-({[5-(1-hydroxycyclopentyl)-1,3,4-oxadiazol-2-yl]amino}methyl)-2H-chromen-2-one;

(R)-6-fluoro-4-(4-fluorophenyl)-7-[({5-[1-hydroxy-1-(trifluoromethyl)propyl]-1,3,4-oxadiazol-2-yl}amino)methyl]-2H-chromen-2-one;

(S)-6-fluoro-4-(4-fluorophenyl)-7-[({5-[1-hydroxy-1-(trifluoromethyl)propyl]-1,3,4-oxadiazol-2-yl}amino)methyl]-2H-chromen-2-one;

6-chloro-4-(4-fluorophenyl)-7-[({5-[1-hydroxy-1-(trifluoromethyl)propyl]-1,3,4-oxadiazol-2-yl}amino)methyl]-2H-chromen-2-one;

6-fluoro-4-(4-fluorophenyl)-7-[({5-[1-hydroxy-1-(trifluoromethyl)propyl]-1,3,4-oxadiazol-2-yl}amino)methyl]-2H-chromen-2-one;

4-(4-fluorophenyl)-7-[({5-[hydroxy(phenyl)methyl]-1,3,4-oxadiazol-2-yl}amino)methyl]-2H-chromen-2-one;

7-({[5-(1-ethyl-1-hydroxypropyl)-1,3,4-oxadiazol-2-yl]amino}methyl)-6-fluoro-4-(4-fluorophenyl)-2H-chromen-2-one;

4-(4-fluorophenyl)-7-({[5-(1-hydroxy-1-methylpropyl)-1,3,4-oxadiazol-2-yl]amino}methyl)-2H-chromen-2-one;

7-({[5-(1-ethylpropyl)-1,3,4-oxadiazol-2-yl]amino}methyl)-4-(4-fluorophenyl)-2H-chromen-2-one;

4-[3-(difluoromethoxy)phenyl]-7-({[5-(1-ethyl-1-hydroxypropyl)-1,3,4-oxadiazol-2-yl]amino}methyl)-2H-chromen-2-one;

4-(4-fluorophenyl)-7-[({5-[1-hydroxy-1-(trifluoromethyl)propyl]-1,3,4-oxadiazol-2-yl}amino)methyl]-2H-chromen-2-one;

(+)-4-(4-fluorophenyl)-7-[({5-[1-hydroxy-1-(trifluoromethyl)propyl]-1,3,4-oxadiazol-2-yl}amino)methyl]-2H-chromen-2-one;

(−)-4-(4-fluorophenyl)-7-[({5-[1-hydroxy-1-(trifluoromethyl)propyl]-1,3,4-oxadiazol-2-yl}amino)methyl]-2H-chromen-2-one;

7-({[5-(1-ethyl-1-hydroxypropyl)-1,3,4-oxadiazol-2-yl]amino}methyl)$_4$-[3-(trifluoromethoxy)phenyl]-2H-chromen-2-one;

6-chloro-7-({[5-(1-ethyl-1-hydroxypropyl)-1,3,4-oxadiazol-2-yl]amino}methyl)-4-phenyl-2H-chromen-2-one;

7-({[5-(1-ethyl-1-hydroxypropyl)-1,3,4-oxadiazol-2-yl]amino}methyl)-4-(3-methylphenyl)-2H-chromen-2-one;

7-(1-{[5-(1-ethyl-1-hydroxypropyl)-1,3,4-oxadiazol-2-yl]amino}ethyl)-4-(4-fluorophenyl)-2H-chromen-2-one;

7-({[5-(1-ethyl-1-fluoropropyl)-1,3,4-oxadiazol-2-yl]amino}methyl)-4-(4-fluorophenyl)-2H-chromen-2-one;

7-{[(5-cyclobutyl-1,3,4-oxadiazol-2-yl)amino]methyl}-4-(4-fluorophenyl)-2H-chromen-2-one;

7-{[(5-cyclopentyl-1,3,4-oxadiazol-2-yl)amino]methyl}-4-(4-fluorophenyl)-2H-chromen-2-one;

7-({[5-(1-ethyl-1-hydroxypropyl)-1,3,4-oxadiazol-2-yl]amino}methyl)-4-(4-fluorophenyl)chroman-2-one;

7-{[[5-(1-ethyl-1-hydroxypropyl)-1,3,4-oxadiazol-2-yl](methyl)amino]methyl}-4-(4-fluorophenyl)-2H-chromen-2-one;

7-({[5-(1-ethyl-1-hydroxypropyl)-1,3,4-oxadiazol-2-yl]amino}methyl)-4-(3-fluorophenyl)-2H-chromen-2-one;

4-(2,4-difluorophenyl)-7-({[5-(1-ethyl-1-hydroxypropyl)-1,3,4-oxadiazol-2-yl]amino}methyl)-2H-chromen-2-one;

7-({[5-(1-ethyl-1-hydroxypropyl)-1,3,4-oxadiazol-2-yl]amino}methyl)-4-(3-methoxyphenyl)-2H-chromen-2-one;

7-({[5-(1-ethyl-1-hydroxypropyl)-1,3,4-oxadiazol-2-yl]amino}methyl)-4-(4-methoxyphenyl)-2H-chromen-2-one;

7-({[5-(1-ethyl-1-hydroxypropyl)-1,3,4-oxadiazol-2-yl]amino}methyl)-4-phenyl-2H-chromen-2-one;

7-[({5-[dicyclopropyl(hydroxy)methyl]-1,3,4-oxadiazol-2-yl}amino)methyl]-4-(4-fluorophenyl)-2H-chromen-2-one;

7-({[5-(1-ethyl-1-hydroxypropyl)-1,3,4-oxadiazol-2-yl]amino}methyl)-4-(4-fluorophenyl)-2H-chromen-2-one;

N-[5-(1-ethyl-1-hydroxypropyl)-1,3,4-oxadiazol-2-yl]-N-{[4-(4-fluorophenyl)-2-oxo-2H-chromen-7-yl]methyl}acetamide;

7-({[5-(1-ethyl-1-hydroxypropyl)-1,3,4-thiadiazol-2-yl]amino}methyl)-4-(4-fluorophenyl)-2H-chromen-2-one;

7-{[(5-tert-butyl-1,3,4-thiadiazol-2-yl)amino]methyl}-4-(4-fluorophenyl)-2H-chromen-2-one;

7-({5-[dicyclopropyl(hydroxy)methyl]-1,3,4-thiadiazol-2-yl}thio)-4-pyridin-3-yl-2H-chromen-2-one;

7-({5-[dicyclopropyl(hydroxy)methyl]-1,3,4-thiadiazol-2-yl}thio)-4-(4-fluorophenyl)-2H-chromen-2-one;

7-{[5-(1-ethyl-1-hydroxypropyl)-1,3,4-thiadiazol-2-yl]thio}-4-(4-fluorophenyl)-2H-chromen-2-one;

or a pharmaceutically acceptable salt or ester thereof.

5. A compound of claim 1 selected from the group consisting of:

4-(4-fluorophenyl)-7-[({5-[1-hydroxy-1-(trifluoromethyl)propyl]-1,3,4-oxadiazol-2-yl}amino)methyl]-6-methyl-2H-chromen-2-one;

4-(4-fluorophenyl)-7-[({5-[(1S)-2,2,2-trifluoro-1-hydroxy-1-methylethyl]-1,3,4-oxadiazol-2-yl}amino)methyl]-2H-chromen-2-one;

3-{7-[({5-[1-hydroxy-1-(trifluoromethyl)propyl]-1,3,4-oxadiazol-2-yl}amino)methyl]-2-oxo-2H-chromen-4-yl}benzonitrile;

6-fluoro-4-(4-fluorophenyl)-7-[({5-[1-hydroxy-1-(trifluoromethyl)propyl]-1,3,4-oxadiazol-2-yl}amino)methyl]-2H-chromen-2-one;

6-chloro-4-(4-fluorophenyl)-7-[({5-[1-hydroxy-1-(trifluoromethyl)propyl]-1,3,4-oxadiazol-2-yl}amino)methyl]-2H-chromen-2-one;

7-({[5-(1-ethyl-1-hydroxypropyl)-1,3,4-oxadiazol-2-yl]amino}methyl)-4-(3-fluorophenyl)-2H-chromen-2-one;

4-(4-fluorophenyl)-7-[({5-[1-hydroxy-1-(trifluoromethyl)propyl]-1,3,4-oxadiazol-2-yl}amino)methyl]-2H-chromen-2-one;

(−)4-(4-fluorophenyl)-7-[({5-[1-hydroxy-1-(trifluoromethyl)propyl]-1,3,4-oxadiazol-2-yl}amino)methyl]-2H-chromen-2-one;

or a pharmaceutically acceptable salt or ester thereof.

6. A pharmaceutical composition comprised of a therapeutically effective amount of a compound of claim 1 and a pharmaceutically acceptable carrier.

7. A pharmaceutical composition comprised of a compound of claim 1, a lipid altering compound and a pharmaceutically acceptable carrier.

8. The compound 4(4-fluorophenyl)-7-[({5-[(1S)-2,2,2-trifluoro-1-hydroxy-1-methylethyl]-1,3,4-oxadiazol-2-yl}amino)methyl]-2H-chromen-2-one.

9. A pharmaceutically acceptable salt or ester of 4-(4-fluorophenyl)-7-[({5-[(1S)-2,2,2-trifluoro-1-hydroxy-1-methylethyl]-1,3,4-oxadiazol-2-yl}amino)methyl]-2H-chromen-2-one.

10. The compound 4-(4-fluorophenyl)-7-[({5-[1-hydroxy-1-(trifluoromethyl)propyl]-1,3,4-oxadiazol-2-yl}amino)methyl]-6-methyl-2H-chromen-2-one.

11. A pharmaceutically acceptable salt or ester of 4-(4-fluorophenyl)-7-[({5-[1-hydroxy-1-(trifluoromethyl)propyl]-1,3,4-oxadiazol-2-yl}amino)methyl]-6-methyl-2H-chromen-2-one.

12. The compound (−) 4-(4-fluorophenyl)-7-{[{5-[1-hydroxy-1-(trifluoromethyl)propyl]-1,3,4-oxadiazol-2-yl}(methyl)amino]methyl}-2H-chromen-2-one.

13. A pharmaceutically acceptable salt or ester of (−) 4-(4-fluorophenyl)-7-{[{5-[1-hydroxy-1-(trifluoromethyl)propyl]-1,3,4-oxadiazol-2-yl}(methyl)amino]methyl}-2H-chromen-2-one.

14. The compound N-{[4-(4-fluorophenyl)-2-oxo-2H-chromen-7-yl]methyl}-N-{5-[1-hydroxy-1-(trifluoromethyl)propyl]-1,3,4-oxadiazol-2-yl}acetamide.

15. A pharmaceutically acceptable ester of N-{[4-(4-fluorophenyl)-2-oxo-2H-chromen-7-yl]methyl}-N-{5-[1-hydroxy-1-(trifluoromethyl)propyl]-1,3,4-oxadiazol-2-yl}acetamide.

16. The compound (S)-6-fluoro-4-(4-fluorophenyl)-7-[({5-[1-hydroxy-1-(trifluoromethyl)propyl]-1,3,4-oxadiazol-2-yl}amino)methyl]-2H-chromen-2-one.

17. A pharmaceutically acceptable salt or ester of (S)-6-fluoro-4-(4-fluorophenyl)-7-[({5-[1-hydroxy-1-(trifluoromethyl)propyl]-1,3,4-oxadiazol-2-yl}amino)methyl]-2H-chromen-2-one.

18. The compound (−)-4-(4-fluorophenyl)-7-[({5-[1-hydroxy-1-(trifluoromethyl)propyl]-1,3,4-oxadiazol-2-yl}amino)methyl]-2H-chromen-2-one.

19. A pharmaceutically acceptable salt or ester of (−)-4-(4-fluorophenyl)-7-[({5-[1-hydroxy-1-(trifluoromethyl)propyl]-1,3,4-oxadiazol-2-yl}amino)methyl]-2H-chromen-2-one.

* * * * *

UNITED STATES PATENT AND TRADEMARK OFFICE
CERTIFICATE OF CORRECTION

PATENT NO. : 7,553,973 B2  Page 1 of 1
APPLICATION NO. : 11/385615
DATED : June 30, 2009
INVENTOR(S) : Marc Blouin et al.

It is certified that error appears in the above-identified patent and that said Letters Patent is hereby corrected as shown below:

Claim 4, column 52, lines 56-58, delete
"4-(4-fluorophenyl)-7-[({5-[1-hydroxy-1-(trifluoromethyl)propyl]-1,3,4-oxadiazol-2-yl}amino)methyl]-6-methyl-2H-chromen-2-one"

Claim 4, column 54, lines 34-39, delete
"7-({5-[dicyclopropyl(hydroxy)methyl]-1,3,4-thiadiazol-2-yl}thio)-4-pyridin-3-yl-2H-chromen-2-one;
7-({5-[dicyclopropyl(hydroxy)methyl]-1,3,4-thiadiazol-2-yl}thio)-4-(4-fluorophenyl)-2H-chromen-2-one;
7-{[5-(1-ethyl-1-hydroxypropyl)-1,3,4-thiadiazol-2-yl]thio}-4-(4-fluorophenyl)-2H-chromen-2-one".

Signed and Sealed this

Twenty-ninth Day of September, 2009

David J. Kappos
*Director of the United States Patent and Trademark Office*